(12) United States Patent
Longo et al.

(10) Patent No.: US 11,219,541 B2
(45) Date of Patent: Jan. 11, 2022

(54) WHEEL LOCK FOR THUMBWHEEL ACTUATED DEVICE

(71) Applicant: Vesper Medical, Inc., Wayne, PA (US)

(72) Inventors: Michael A. Longo, Glenmoore, PA (US); Timothy W. O'Neil, King of Prussia, PA (US); Christopher John Turek, West Chester, PA (US)

(73) Assignee: Vesper Medical, Inc., Wayne, PA (US)

( * ) Notice: Subject to any disclaimer, the term of this patent is extended or adjusted under 35 U.S.C. 154(b) by 0 days.

(21) Appl. No.: 16/880,528

(22) Filed: May 21, 2020

(65) Prior Publication Data
US 2021/0361453 A1   Nov. 25, 2021

(51) Int. Cl.
| | | |
|---|---|---|
| *A61F 2/95* | (2013.01) | |
| *A61F 2/966* | (2013.01) | |
| *A61M 25/01* | (2006.01) | |

(52) U.S. Cl.
CPC ............ *A61F 2/966* (2013.01); *A61F 2/9517* (2020.05); *A61M 25/0113* (2013.01)

(58) Field of Classification Search
CPC ........ A61F 2/2427; A61F 2/2436; A61F 2/95; A61F 2/9517; A61F 2/962; A61F 2/966; A61B 17/1227; A61B 17/326; A61B 2017/00446; A61B 2017/00451; A61M 25/0113; Y10T 24/1391; Y10T 24/1394; F16L 33/035; F16D 63/006
USPC ........................................ 74/577 SF; 70/190
See application file for complete search history.

(56) References Cited

U.S. PATENT DOCUMENTS

| | | | | |
|---|---|---|---|---|
| 2,885,758 | A | * | 5/1959 | Russo ...................... D06F 55/02 24/531 |
| 3,913,187 | A | * | 10/1975 | Okuda ...................... F16L 3/12 24/484 |
| 4,665,918 | A | | 5/1987 | Garza et al. |
| 5,305,978 | A | * | 4/1994 | Current ................. F16L 3/1075 248/230.4 |
| 5,415,664 | A | | 5/1995 | Pinchuk |
| 5,417,708 | A | | 5/1995 | Hall et al. |

(Continued)

FOREIGN PATENT DOCUMENTS

| | | |
|---|---|---|
| DE | 29717110 U1 | 11/1997 |
| DE | 19819634 | 11/1999 |

(Continued)

OTHER PUBLICATIONS

International Search Report and Written Opinion issued for Application No. PCT/US2019/034371, dated Aug. 19, 2019.

(Continued)

*Primary Examiner* — Diane D Yabut
*Assistant Examiner* — Christian D Knauss
(74) *Attorney, Agent, or Firm* — Meunier Carlin & Curfman LLC

(57) ABSTRACT

A wheel lock or clip for maintaining position of a thumbwheel or wheel of a rotary actuated delivery device includes an arcuate or curved body having a live hinge extending therefrom, the hinge connected to an arm having an engagement tooth extending therefrom. The tooth is operatively connected to tab for actuation by a user to disengage the engagement tooth from teeth of gear or barrel of a wheel or a thumbwheel of the rotary actuated device to thereby allow free movement of the wheel or thumbwheel.

11 Claims, 26 Drawing Sheets

(56) References Cited

U.S. PATENT DOCUMENTS

| | | |
|---|---|---|
| 5,433,723 A | 7/1995 | Lindenberg et al. |
| 5,443,477 A | 8/1995 | Marin et al. |
| 5,458,615 A | 10/1995 | Klemm et al. |
| 5,484,444 A | 1/1996 | Braunschweiler et al. |
| 5,501,654 A | 3/1996 | Failla et al. |
| 5,507,768 A | 4/1996 | Lau et al. |
| 5,571,168 A | 11/1996 | Toro |
| 5,695,499 A | 12/1997 | Helgerson et al. |
| 5,725,534 A | 3/1998 | Rasmussen et al. |
| 5,759,186 A | 6/1998 | Bachmann et al. |
| 5,788,707 A | 8/1998 | Del Toro et al. |
| 5,800,517 A | 9/1998 | Anderson et al. |
| 5,860,998 A | 1/1999 | Robinson et al. |
| 5,906,619 A | 5/1999 | Olson et al. |
| 5,944,727 A | 8/1999 | Ahari et al. |
| 6,019,778 A | 2/2000 | Wilson et al. |
| 6,113,608 A | 9/2000 | Monroe et al. |
| 6,117,140 A | 9/2000 | Munsinger |
| 6,164,605 A * | 12/2000 | Drake .................. B60T 17/046 24/16 PB |
| 6,165,166 A | 12/2000 | Samuelson et al. |
| 6,203,550 B1 | 3/2001 | Olson |
| 6,241,758 B1 | 6/2001 | Cox et al. |
| 6,299,635 B1 | 10/2001 | Frantzen |
| 6,302,893 B1 | 10/2001 | Limon et al. |
| 6,402,760 B1 | 6/2002 | Fedida |
| 6,599,296 B1 | 7/2003 | Gillick et al. |
| 6,613,075 B1 | 9/2003 | Healy et al. |
| 6,620,550 B2 | 9/2003 | Christian et al. |
| 6,669,716 B1 | 12/2003 | Gilson et al. |
| 6,702,846 B2 | 3/2004 | Mikus et al. |
| 6,755,854 B2 | 6/2004 | Gillick et al. |
| 6,866,669 B2 | 3/2005 | Buzzard et al. |
| 6,911,039 B2 | 6/2005 | Shiu et al. |
| 6,939,352 B2 | 9/2005 | Buzzard et al. |
| 7,033,368 B2 | 4/2006 | Rourke |
| 7,052,511 B2 | 5/2006 | Weldon et al. |
| 7,105,016 B2 | 9/2006 | Shiu et al. |
| 7,182,779 B2 | 2/2007 | Acosta et al. |
| 7,278,998 B2 | 10/2007 | Gaschino et al. |
| 7,300,456 B2 | 11/2007 | Andreas et al. |
| 7,309,350 B2 | 12/2007 | Landreville et al. |
| 7,326,236 B2 | 2/2008 | Andreas et al. |
| 7,381,216 B2 | 6/2008 | Buzzard et al. |
| D576,725 S | 9/2008 | Shumer et al. |
| 7,419,501 B2 | 9/2008 | Chiu et al. |
| D578,216 S | 10/2008 | Dorn et al. |
| D578,643 S | 10/2008 | Shumer et al. |
| D578,644 S | 10/2008 | Shumer et al. |
| D578,645 S | 10/2008 | Shumer et al. |
| 7,476,244 B2 | 1/2009 | Buzzard et al. |
| 7,550,001 B2 | 6/2009 | Dorn et al. |
| 7,553,322 B2 | 6/2009 | Dorn et al. |
| 7,553,324 B2 | 6/2009 | Andreas et al. |
| 7,660,621 B2 | 2/2010 | Skakoon et al. |
| 7,674,282 B2 | 3/2010 | Wu et al. |
| 7,758,625 B2 | 7/2010 | Wu et al. |
| 7,780,716 B2 | 8/2010 | Pappas et al. |
| 7,794,489 B2 | 9/2010 | Shumer et al. |
| 7,799,065 B2 | 9/2010 | Pappas et al. |
| 7,815,669 B2 | 10/2010 | Matsuoka et al. |
| 7,819,882 B2 | 10/2010 | Rourke |
| 7,892,274 B2 | 2/2011 | Will et al. |
| 7,935,141 B2 | 5/2011 | Randall et al. |
| 7,963,987 B2 | 6/2011 | Melsheimer et al. |
| 7,967,829 B2 | 6/2011 | Gunderson et al. |
| 7,976,574 B2 | 7/2011 | Papp |
| 7,993,384 B2 | 8/2011 | Wu et al. |
| 8,016,870 B2 | 9/2011 | Chew |
| 8,062,344 B2 | 11/2011 | Dorn et al. |
| 8,075,607 B2 | 12/2011 | Melsheimer |
| 8,092,468 B2 | 1/2012 | Hansen |
| 8,157,851 B2 | 4/2012 | Andreas |
| 8,177,831 B2 | 5/2012 | Andreas |
| 8,216,296 B2 | 7/2012 | Wu et al. |
| 8,382,813 B2 | 2/2013 | Shumer |
| D678,512 S | 3/2013 | Bow |
| 8,416,636 B2 | 4/2013 | Carman et al. |
| 8,419,784 B2 | 4/2013 | Matsuoka et al. |
| 8,486,128 B2 | 7/2013 | Jen et al. |
| 8,500,789 B2 | 8/2013 | Wueebbeling et al. |
| 8,500,792 B2 | 8/2013 | Berra |
| 8,585,747 B2 | 11/2013 | Andreas et al. |
| 8,778,006 B2 | 7/2014 | Fargahi et al. |
| 8,784,468 B2 | 7/2014 | Gerdts et al. |
| 8,808,346 B2 | 8/2014 | Jimenez, Jr. et al. |
| 8,828,072 B2 | 9/2014 | Hoffman et al. |
| 8,852,266 B2 | 10/2014 | Brooks et al. |
| 8,864,811 B2 | 10/2014 | Kao |
| 8,888,834 B2 | 11/2014 | Hansen et al. |
| 8,911,487 B2 | 12/2014 | Bennett et al. |
| 8,951,297 B2 | 2/2015 | Kawakita |
| 8,956,398 B2 | 2/2015 | George et al. |
| 8,986,362 B2 | 3/2015 | Snow et al. |
| 8,986,363 B2 | 3/2015 | McHugo et al. |
| 9,039,750 B2 | 5/2015 | Ryan et al. |
| 9,138,315 B2 | 9/2015 | Straubinger et al. |
| 9,149,379 B2 | 10/2015 | Keady et al. |
| 9,301,864 B2 | 4/2016 | Kao |
| 9,314,360 B2 | 4/2016 | Kao |
| 9,320,591 B2 | 4/2016 | Bolduc |
| 9,408,736 B2 | 8/2016 | Loewen |
| 9,421,115 B2 | 8/2016 | Wübbeling et al. |
| 9,445,928 B2 | 9/2016 | Argentine |
| 9,539,130 B2 | 1/2017 | Farag et al. |
| D779,053 S | 2/2017 | Kobida et al. |
| 9,566,179 B2 | 2/2017 | Andreas et al. |
| 9,622,894 B2 | 4/2017 | McGee |
| D786,429 S | 5/2017 | Cummins et al. |
| 9,662,236 B2 | 5/2017 | Masubuchi |
| 9,675,486 B2 | 6/2017 | Jimenez, Jr. et al. |
| D795,425 S | 8/2017 | Cummins |
| 9,744,021 B2 | 8/2017 | Bolduc |
| 9,765,858 B2 | 9/2017 | Kelly |
| 9,849,016 B2 | 12/2017 | Beard et al. |
| 9,872,785 B2 | 1/2018 | Dorn et al. |
| 9,878,127 B2 | 1/2018 | Damm et al. |
| 9,901,468 B2 | 2/2018 | Harada |
| 9,913,741 B2 | 3/2018 | Melsheimer et al. |
| 9,918,835 B2 | 3/2018 | Guyenot et al. |
| 9,974,677 B2 | 5/2018 | Costello |
| 9,974,678 B2 | 5/2018 | Cummins |
| 10,016,292 B2 | 7/2018 | Senness et al. |
| 10,441,449 B1 | 10/2019 | Longo et al. |
| 10,449,073 B1 | 10/2019 | Longo et al. |
| 2001/0004696 A1 | 6/2001 | Roberts et al. |
| 2001/0012944 A1 | 8/2001 | Bicek et al. |
| 2001/0027323 A1 | 10/2001 | Sullivan et al. |
| 2001/0047150 A1 | 11/2001 | Chobotov |
| 2002/0007138 A1 | 1/2002 | Wilk et al. |
| 2002/0007206 A1 | 1/2002 | But et al. |
| 2002/0029075 A1 | 3/2002 | Leonhardt |
| 2002/0065545 A1 | 5/2002 | Leonhardt |
| 2002/0128707 A1 | 9/2002 | Kavteladze |
| 2002/0151953 A1 | 10/2002 | Chobotov et al. |
| 2003/0009174 A1 | 1/2003 | Smith |
| 2003/0036791 A1 | 2/2003 | Philipp et al. |
| 2003/0040789 A1 | 2/2003 | Colgan et al. |
| 2003/0045893 A1 | 3/2003 | Ginn |
| 2003/0050686 A1 | 3/2003 | Raeder-Devens et al. |
| 2003/0074045 A1 | 4/2003 | Buzzard et al. |
| 2003/0120331 A1 | 6/2003 | Chobotov et al. |
| 2003/0149469 A1 | 8/2003 | Wolinsky et al. |
| 2003/0149476 A1 | 8/2003 | Damm et al. |
| 2003/0149478 A1 | 8/2003 | Figulla et al. |
| 2003/0153941 A1 | 8/2003 | Rourke |
| 2003/0167087 A1 | 9/2003 | Piplani et al. |
| 2003/0191516 A1 | 10/2003 | Weldon et al. |
| 2004/0006380 A1 | 1/2004 | Buck et al. |
| 2004/0093056 A1 | 5/2004 | Johnson et al. |
| 2004/0106977 A1 | 6/2004 | Sullivan et al. |
| 2004/0153137 A1 | 8/2004 | Gaschino et al. |
| 2004/0167619 A1 | 8/2004 | Case et al. |
| 2004/0181239 A1 | 9/2004 | Dorn et al. |

(56) References Cited

U.S. PATENT DOCUMENTS

| | | |
|---|---|---|
| 2004/0193243 A1 | 9/2004 | Mangiardi et al. |
| 2004/0199240 A1 | 10/2004 | Dorn |
| 2004/0210188 A1 | 10/2004 | Glines et al. |
| 2005/0027345 A1 | 2/2005 | Horan et al. |
| 2005/0033403 A1 | 2/2005 | Ward et al. |
| 2005/0038493 A1 | 2/2005 | Feeser |
| 2005/0060016 A1 | 3/2005 | Wu et al. |
| 2005/0080476 A1 | 4/2005 | Gunderson et al. |
| 2005/0090887 A1 | 4/2005 | Pryor |
| 2005/0090890 A1 | 4/2005 | Wu et al. |
| 2005/0137686 A1 | 6/2005 | Salahieh et al. |
| 2005/0149159 A1 | 7/2005 | Andreas et al. |
| 2005/0149160 A1 | 7/2005 | McFerran |
| 2005/0182475 A1 | 8/2005 | Jen et al. |
| 2005/0232961 A1 | 10/2005 | Lowe et al. |
| 2005/0256562 A1 | 11/2005 | Clerc et al. |
| 2005/0273151 A1 | 12/2005 | Fulkerson et al. |
| 2005/0288763 A1 | 12/2005 | Andreas et al. |
| 2006/0009833 A1 | 1/2006 | Chobotov et al. |
| 2006/0020321 A1 | 1/2006 | Parker |
| 2006/0142833 A1 | 6/2006 | Von Oepen et al. |
| 2006/0212105 A1 | 9/2006 | Dorn et al. |
| 2006/0229711 A1 | 10/2006 | Yan et al. |
| 2006/0247661 A1 | 11/2006 | Richards et al. |
| 2006/0259124 A1 | 11/2006 | Matsuoka et al. |
| 2006/0286145 A1 | 12/2006 | Horan et al. |
| 2007/0055340 A1 | 3/2007 | Pryor |
| 2007/0060999 A1 | 3/2007 | Randall et al. |
| 2007/0088421 A1 | 4/2007 | Loewen |
| 2007/0100440 A1 | 5/2007 | Figulla et al. |
| 2007/0112355 A1 | 5/2007 | Salahieh et al. |
| 2007/0118079 A1 | 5/2007 | Moberg et al. |
| 2007/0142906 A1 | 6/2007 | Figulla et al. |
| 2007/0156224 A1 | 7/2007 | Cioanta et al. |
| 2007/0162127 A1 | 7/2007 | Peterman et al. |
| 2007/0168014 A1 | 7/2007 | Jimenez et al. |
| 2007/0185558 A1 | 8/2007 | Hartley |
| 2007/0191925 A1 | 8/2007 | Dorn |
| 2007/0213813 A1 | 9/2007 | Von Segesser et al. |
| 2007/0219617 A1 | 9/2007 | Saint |
| 2008/0082154 A1 | 4/2008 | Tseng et al. |
| 2008/0154293 A1 | 6/2008 | Taylor |
| 2008/0188920 A1 | 8/2008 | Moberg et al. |
| 2008/0255660 A1 | 10/2008 | Guyenot et al. |
| 2009/0005760 A1 | 1/2009 | Cartledge et al. |
| 2009/0024133 A1 | 1/2009 | Keady et al. |
| 2009/0024137 A1 | 1/2009 | Chuter et al. |
| 2009/0171428 A1 | 7/2009 | Hansen |
| 2009/0177264 A1 | 7/2009 | Ravenscroft |
| 2009/0210046 A1 | 8/2009 | Shumer et al. |
| 2009/0216310 A1 | 8/2009 | Straubinger et al. |
| 2009/0234443 A1 | 9/2009 | Ottma et al. |
| 2009/0312831 A1 | 12/2009 | Dorn |
| 2010/0004606 A1 | 1/2010 | Hansen et al. |
| 2010/0004730 A1 | 1/2010 | Benjamin et al. |
| 2010/0036472 A1 | 2/2010 | Papp |
| 2010/0076541 A1 | 3/2010 | Kumoyama |
| 2010/0125280 A1 | 5/2010 | Molloy |
| 2010/0137967 A1 | 6/2010 | Atlani et al. |
| 2010/0168756 A1 | 7/2010 | Dorn et al. |
| 2010/0168834 A1 | 7/2010 | Ryan et al. |
| 2010/0174290 A1 | 7/2010 | Wueebbeling et al. |
| 2010/0292779 A1 | 11/2010 | Straubinger et al. |
| 2011/0056064 A1 | 3/2011 | Malewicz et al. |
| 2011/0190862 A1 | 8/2011 | Bashiri et al. |
| 2011/0190865 A1 | 8/2011 | McHugo et al. |
| 2011/0288626 A1 | 11/2011 | Straubinger et al. |
| 2011/0295363 A1 | 12/2011 | Girard et al. |
| 2011/0319989 A1 | 12/2011 | Lane et al. |
| 2012/0022631 A1 | 1/2012 | Costello |
| 2012/0022632 A1 | 1/2012 | Hoffman et al. |
| 2012/0022635 A1 | 1/2012 | Yamashita |
| 2012/0029607 A1 | 2/2012 | McHugo et al. |
| 2012/0041450 A1 | 2/2012 | Awtar et al. |
| 2012/0053671 A1 | 3/2012 | McHugo et al. |
| 2012/0116493 A1 | 5/2012 | Harada | |
| 2012/0123516 A1* | 5/2012 | Gerdts .................. A61F 2/966 623/1.12 |
| 2012/0158117 A1 | 6/2012 | Ryan |
| 2012/0209175 A1 | 8/2012 | Moelgaard-Nielsen |
| 2012/0209366 A1 | 8/2012 | Sudo et al. |
| 2012/0226341 A1 | 9/2012 | Schreck et al. |
| 2012/0265288 A1 | 10/2012 | Jones et al. |
| 2012/0310321 A1 | 12/2012 | Beach et al. |
| 2012/0330401 A1 | 12/2012 | Sugimoto et al. |
| 2013/0013057 A1 | 1/2013 | Salahieh et al. |
| 2013/0018451 A1 | 1/2013 | Grabowski et al. |
| 2013/0079864 A1 | 3/2013 | Boden et al. |
| 2013/0085562 A1 | 4/2013 | Rincon et al. |
| 2013/0103130 A1 | 4/2013 | Lubinski et al. |
| 2013/0184805 A1 | 7/2013 | Sawada |
| 2013/0211493 A1 | 8/2013 | Wubbeling et al. |
| 2013/0268048 A1 | 10/2013 | Watson et al. |
| 2013/0268049 A1 | 10/2013 | Munsinger et al. |
| 2013/0304189 A1 | 11/2013 | Shimoyama |
| 2013/0338752 A1 | 12/2013 | Geusen et al. |
| 2014/0025155 A1 | 1/2014 | Masubuchi |
| 2014/0081252 A1 | 3/2014 | Bowe et al. |
| 2014/0107673 A1 | 4/2014 | Snyder et al. |
| 2014/0121674 A1 | 5/2014 | Staunton |
| 2014/0121755 A1 | 5/2014 | Farag et al. |
| 2014/0180380 A1 | 6/2014 | Kelly |
| 2014/0257454 A1 | 9/2014 | McGee |
| 2014/0257459 A1 | 9/2014 | Masakazu |
| 2014/0276682 A1 | 9/2014 | Hendrick et al. |
| 2014/0277037 A1 | 9/2014 | Grace et al. |
| 2014/0277321 A1 | 9/2014 | Grace |
| 2014/0277349 A1 | 9/2014 | Vad |
| 2014/0343601 A1 | 11/2014 | Abbott et al. |
| 2014/0343660 A1 | 11/2014 | Shimoyama |
| 2015/0025615 A1 | 1/2015 | Brooks et al. |
| 2015/0051688 A1 | 2/2015 | Cummins |
| 2015/0057739 A1 | 2/2015 | Costello |
| 2015/0057741 A1 | 2/2015 | Ryan |
| 2015/0065280 A1 | 3/2015 | Kelly |
| 2015/0094794 A1 | 4/2015 | Cummins et al. |
| 2015/0105796 A1 | 4/2015 | Grace |
| 2015/0119800 A1 | 4/2015 | Neoh et al. |
| 2015/0127092 A1 | 5/2015 | Straubinger et al. |
| 2015/0148894 A1 | 5/2015 | Damm et al. |
| 2015/0230954 A1 | 8/2015 | McHugo |
| 2015/0238315 A1 | 8/2015 | Rabito et al. |
| 2015/0238730 A1 | 8/2015 | Corman et al. |
| 2015/0250631 A1 | 9/2015 | Cummins et al. |
| 2015/0265445 A1 | 9/2015 | Weber et al. |
| 2015/0282881 A1 | 10/2015 | Beard et al. |
| 2015/0297378 A1 | 10/2015 | Senness et al. |
| 2015/0335333 A1 | 11/2015 | Jones et al. |
| 2015/0343121 A1 | 12/2015 | Kobida et al. |
| 2016/0074184 A1 | 3/2016 | Cummins et al. |
| 2016/0074189 A1 | 3/2016 | Cummins |
| 2016/0123441 A1 | 5/2016 | Gillick et al. |
| 2016/0135972 A1 | 5/2016 | Vad et al. |
| 2016/0135975 A1 | 5/2016 | Shimoyama |
| 2016/0158010 A1 | 6/2016 | Lim et al. |
| 2016/0158049 A1 | 6/2016 | Dooley |
| 2016/0213465 A1 | 7/2016 | Girard et al. |
| 2016/0235568 A1 | 8/2016 | Green |
| 2016/0262883 A1 | 9/2016 | Sandstrom |
| 2016/0303734 A1 | 10/2016 | Bowles et al. |
| 2017/0035590 A1 | 2/2017 | Watson et al. |
| 2017/0348100 A1 | 2/2017 | Lane et al. |
| 2017/0056156 A1 | 3/2017 | Ryan |
| 2017/0095236 A1 | 4/2017 | Sharma et al. |
| 2017/0095330 A1 | 4/2017 | Malewicz et al. |
| 2017/0095922 A1 | 4/2017 | Licht et al. |
| 2017/0172773 A1 | 6/2017 | Gong et al. |
| 2017/0216063 A1 | 8/2017 | Bessho |
| 2017/0348087 A1 | 12/2017 | Chobotov et al. |
| 2018/0021132 A1 | 1/2018 | Ottma et al. |
| 2018/0080533 A1 | 3/2018 | Awtar |
| 2018/0098849 A1 | 4/2018 | Yellin et al. |
| 2018/0133006 A1 | 5/2018 | Jones et al. |
| 2018/0133007 A1 | 5/2018 | Prabhu |

(56) References Cited

U.S. PATENT DOCUMENTS

| | | | |
|---|---|---|---|
| 2018/0147076 A1 | 5/2018 | Cummins et al. |
| 2018/0153693 A1 | 6/2018 | Copeland et al. |
| 2018/0153694 A1 | 6/2018 | Wilson et al. |
| 2018/0206976 A1 | 7/2018 | Cartledge et al. |

FOREIGN PATENT DOCUMENTS

| | | |
|---|---|---|
| DE | 102013015896 | 3/2015 |
| EP | 3354237 | 8/2018 |
| JP | 2008132027 | 6/2008 |
| JP | 2012187177 | 10/2012 |
| KR | 101685325 | 12/2016 |
| WO | 2008034793 | 3/2008 |
| WO | 2008124844 | 10/2008 |
| WO | 2017052414 | 3/2017 |
| WO | 2017136778 A9 | 8/2017 |
| WO | 2018107123 | 6/2018 |

OTHER PUBLICATIONS

International Search Report and Written Opinion issued for Application No. PCT/US2019/034376, dated Oct. 30, 2019.
Notification of Transmittal of the International Search Report and the Written Opinion of the International Search Authority, dated Aug. 16, 2021 (12 pages).

\* cited by examiner

WHEEL LOCK FOR THUMBWHEEL ACTUATED DEVICE

BACKGROUND OF THE INVENTION

Field of the Invention

Embodiments of the present invention relate to a stent delivery device, specifically a single-handed thumbwheel driven delivery handle.

Background

There are a number of medical conditions and procedures in which a device such as a stent is placed in the body to create or maintain a passage. There are a wide variety of stents used for different purposes, from expandable coronary, vascular and biliary stents, to plastic stents used to allow the flow of urine between kidney and bladder.

Self-expanding stents, as well as balloon expandable stents, may also be used to treat various issues with the vascular system, including, but not limited to May-Thurner Syndrome and Deep Vein Thrombosis.

Stents are usually delivered in a compressed condition to the target site and then, deployed at that location into an expanded condition to support the vessel and help maintain it in an open position. The delivery system used to implant or deploy at the stent target site in the diseased vessel using a delivery system.

Stents are commonly delivered using a catheter delivery system. A common type of delivery system for delivering a self-expanding stent is called a pull back delivery system. This type of delivery system utilizes two catheters or shafts which are concentrically arranged, one around another. The stent is carried axially around the distal end of the inner catheter or shaft. The stent is carried to the delivery site on the distal end of the delivery device, held in its compressed delivery position by the outer shaft or catheter. Once at the desired placement site, the outer shaft is pulled back, releasing the stent to self-expand.

In another aspect, thumbwheel actuated delivery systems may be used to deliver the stent to its desired location. These devices are often preloaded with the stent for delivery such that unwanted actuation of the delivery device, particularly a thumbwheel actuated device, will compromise the ability to use the delivery system as designed. Accordingly, there is a need for a mechanism for preventing unwanted actuation of the actuation member, such as a thumbwheel, on a stent delivery system

BRIEF SUMMARY

Accordingly, the present invention is directed to a wheel lock for thumbwheel actuated device that obviates one or more of the problems due to limitations and disadvantages of the related art.

In accordance with the purpose(s) of this invention, as embodied and broadly described herein, a clip for reducing motion of a wheel having a plurality of teeth on an outer circumference thereof, the plurality of teeth having grooves of predetermined shape and size therebetween, includes a body; an arm connected to and extending from the body, the arm comprising a bent portion and an extending portion, such that arm is movable toward and away from the body with the bent portion having hinge-like properties; an engagement tooth extending from the arm and sized to be received in at least one of the grooves between two of said plurality of teeth of said wheel; and a tab operatively connected to the engagement tooth such that motion of the tab causes the engagement tooth to disengage from the plurality of teeth of said wheel.

In another aspect of the present invention, a kit includes a wheel actuated device having a wheel having a plurality of gear-like teeth with grooves therebetween around at least portion of the circumference of the wheel; an axle about which the wheel is movable; and a housing, the wheel at least partially within the housing and having a portion of the wheel extending above the housing; and a removable wheel lock, having a body; an arm connected to and extending from the body, the arm comprising a bent portion and an extending portion, such that arm is movable toward and away from the body with the bent portion having hinge-like properties; an engagement tooth extending from the arm and received in at least one of the grooves between two of the gear-like teeth of the wheel; and a tab operatively connected to the engagement tooth such that motion of the tab causes the engagement tooth to disengage from the plurality of teeth of said wheel.

Additional advantages will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

Further embodiments, features, and advantages of the rotary handle stent delivery system and method, as well as the structure and operation of the various embodiments of the rotary handle stent delivery system and method, are described in detail below with reference to the accompanying drawings.

It is to be understood that both the foregoing general description and the following detailed description are exemplary and explanatory only and are not restrictive of the invention as claimed.

BRIEF DESCRIPTION OF THE DRAWINGS

The accompanying figures, which are incorporated herein and form part of the specification, illustrate a wheel lock for thumbwheel actuated device. Together with the description, the figures further serve to explain the principles of the rotary handle stent delivery system and method described herein and thereby enable a person skilled in the pertinent art to make and use the rotary handle stent delivery system and method.

Reference will now be made to the accompanying drawings, which are not necessarily drawn to scale. The patent or application file contains at least one drawing executed in color. Copies of this patent or patent application publication with the color drawing(s) will be provided by the Office upon request and payment of the necessary fee.

DETAILED DESCRIPTION

Reference will now be made in detail to embodiments of the wheel lock for thumbwheel actuated device with reference to the accompanying figures. Various embodiments disclosed herein illustrate a device and associated method for delivering expandable stents or other medical devices to implant or deploy a stent or other medical device to a target site in the diseased vessel. Exemplary thumbwheel actuation delivery devices are described in U.S. Pat. Nos. 10,441,449 and 10,449,073, which are hereby incorporated by reference as if fully set forth herein. Although the wheel lock for thumbwheel actuated device is described with reference to the stent delivery devices of U.S. Pat. Nos. 10,441,449 and 10,449,073, such wheel lock as described herein may be used with any wheel/thumbwheel actuated device, including, but not limited to, stent delivery devices.

Figure 1A:
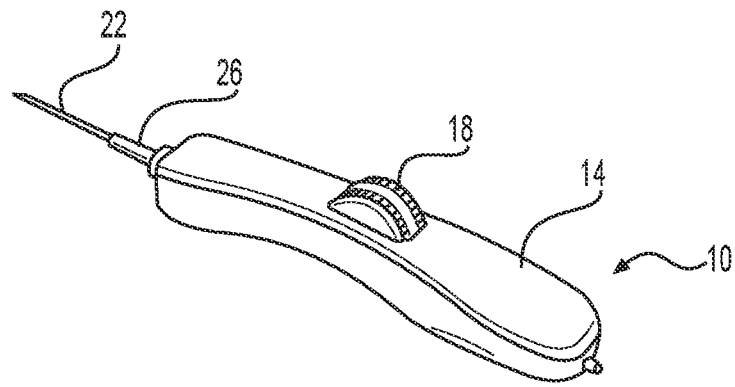
FIGS. 1A, 1B and 1C show various embodiments of an examplestent delivery handle.
Figure 1B:
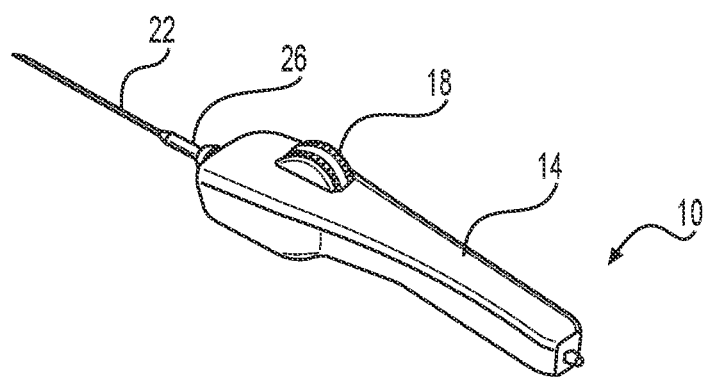
Figure 1C:
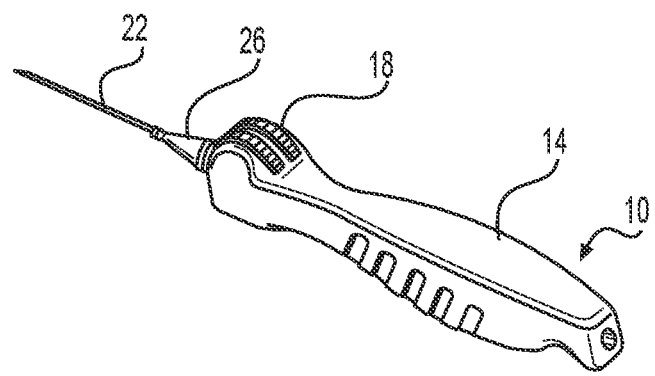
Figure 2:
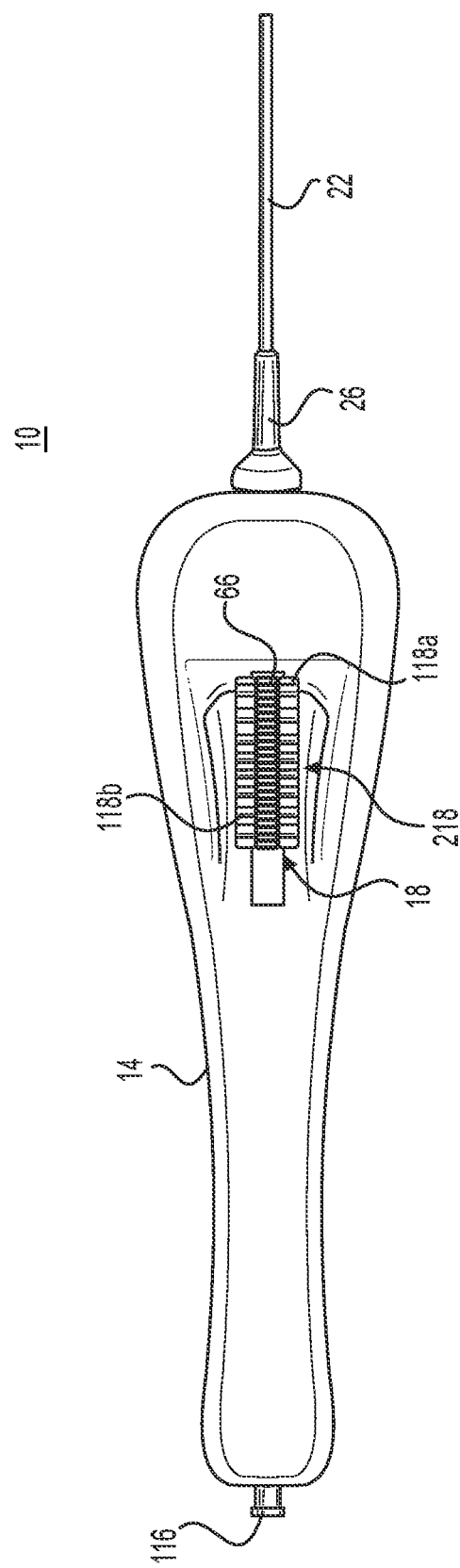
FIG. 2 is a top view of the example stent delivery handle of FIG. 1.

FIGS. 1A, 1B and 1C show various embodiments of a stent delivery handle. As illustrated, the handle 10 includes a housing 14 and a thumbwheel/thumbwheel assembly 18, with a catheter 22 extending therefrom. FIG. 2 is a top view of an exemplary embodiment of the delivery handle of FIG. 1. In the embodiment illustrated in FIG. 2, the delivery handle 10 has a thumbwheel assembly having two thumb wheels 118a and 118b (e.g., a dual disk thumbwheel assembly) and an inner barrel 66. As illustrated, the handle 210 includes a housing 14 and a thumbwheel/thumbwheel assembly 218, with a catheter 222 extending therefrom. The thumbwheel assembly may include a single unit having the inner barrel contiguous with one or both of the thumbwheel or may be separate parts. The thumbwheel assembly may have only one thumbwheel. The thumbwheel assembly 218 in the illustrated embodiment of FIG. 2 includes two thumb wheels, 118a and 118b and inner barrel 66. As can be seen in FIG. 2, the inner barrel 66 includes a scalloped or toothed surface. The toothed surface may be designed, or pitched, to engage timing belt or other mechanism for transferring motion of the thumbwheel to drive the device, as can be seen in various embodiments herein. For example, the inner barrel may have barrel teeth having a pitch corresponding to a drive belt or screw to cause movement of the drive belt or screw when the thumbwheel is actuated, the barrel teeth having a groove or recess between adjacent teeth. However, the scope of the invention described herein is not limited to a particular deliver mechanism, and may be applied to any wheel driven device having a toothed thumbwheel assembly, as described herein.

Figure 3A:
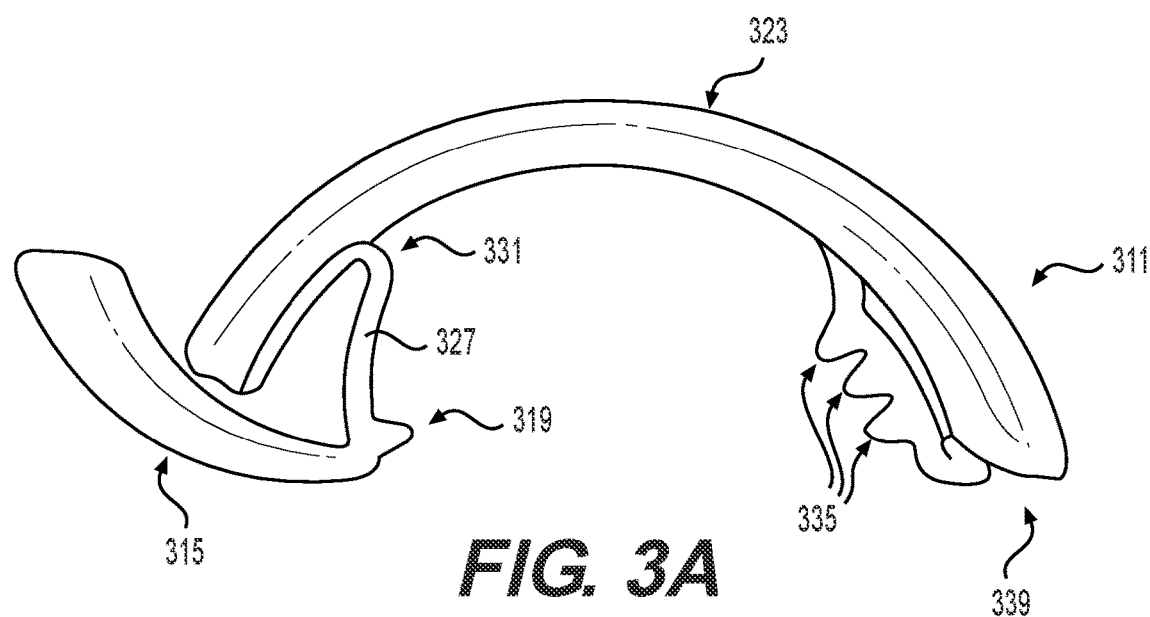
FIG. 3A shows an exemplary wheel lock or locking tab according to principles described herein for use with a wheel/thumbwheel actuated system or device.
Figure 3B:
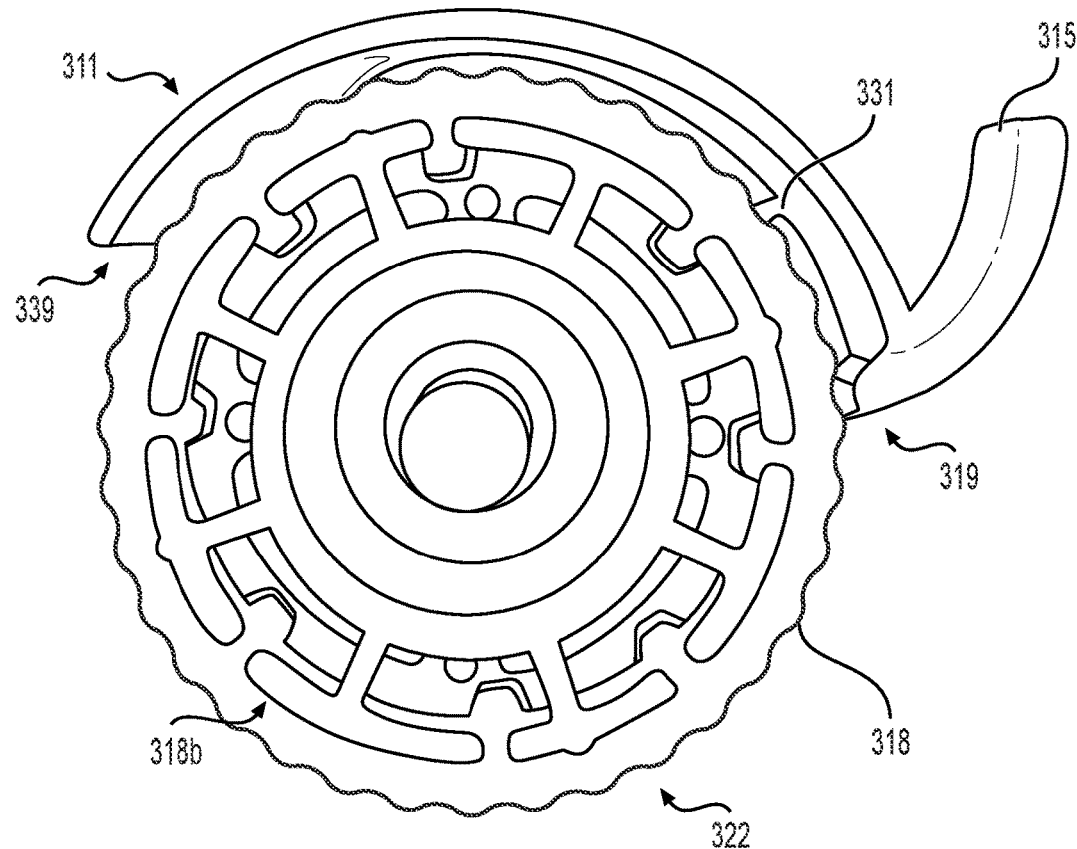
FIG. 3B shows a side view of the exemplary wheel lock or clip with respect to a wheel to be locked.
Figure 4A:
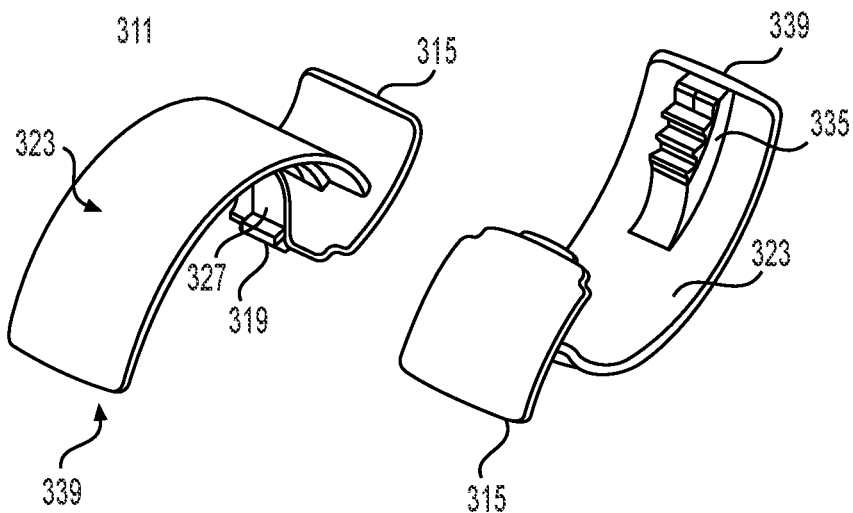
FIG. 4A is a perspective drawing of the wheel lock/clip in a disengaged state.

FIG. 3A shows an exemplary wheel lock or locking tab 311 for use with a wheel/thumbwheel actuated system or device (not shown). FIG. 3B shows a side view the exemplary wheel lock or clip 311 with respect to a wheel 318 to be locked. As will be appreciated, in FIGS. 3A and 3B the elements are shown separated from a wheel actuated device for the purposes of explanation. The present device may be used in combination with any wheel actuated device where it would be appropriate to prevent motion of the wheel in various circumstances. As shown, the exemplary wheel lock 311 includes a tab 315 that, when pulled, allows for disengagement of at least one engagement tooth 319 of the wheel lock 311 from the wheel 318. In addition to the tab 315 and the engagement tooth 319, the wheel lock/clip 311 includes a body 323, an arm 326 having an extending portion 327 and a u-shaped or bent portion 331. The u-shaped bent portion 331 exhibits hinge-like behavior and may be a living hinge, but may also another structure that imparts and outward force on the extending portion 327 urge the substantially straight portion away from the body 323. The body 323 may be arcuate or curved to emulate the curved shape of the wheel/wheel assembly 318. The arm 326 extends from the body 323 via the bent portion 331. The tab 315 is connected to the arm 326, an end portion of the tab 315 extending past an end of the body 323 to allow a user to access the tab 315 to move the tab 315 in a desired direction. As illustrated in the figures, the tab 315 may extend from end of the extending portion 327 at and end opposite the bent portion 331. The engagement tooth 319 extends from a portion of the extending portion 327 in a direction such that movement of the tab 315 by a user will cause the engagement tooth 319 to disengage from a complementary set of barrel teeth (e.g., a set of teeth spaced apart to receive the engagement tooth 319 therebetween) on an outer periphery of the inner barrel 66 (not shown in FIG. 3B). Additional teeth 335 may be provided to the inner side of the arcuate clip body to provide an additional engagement location of the wheel lock/clip to the wheel/wheel assembly 318. The additional teeth 335 are sized to be complementary to and engage with the barrel teeth on an outer periphery of the inner barrel. These additional teeth 335 also provide a bite at a predetermined point on the wheel to help with the wheel lock/clip being removed at a proper location to reduce movement of the wheel/thumbwheel during removal. While three additional teeth 335 are shown in FIG. 3A, more or fewer, or even no, additional teeth may be included in the device. FIG. 3A further shows a cavity between the additional teeth 335 and an inner surface of the clip body 323. Such cavity may be omitted from the wheel lock/clip 311. FIG. 4A is a perspective drawing of the wheel lock/clip 311 in a disengaged state.

The wheel lock/clip 318, as thus described, itself acts as a living hinge, which is in tension when applied to the inner barrel and relaxed when disengaged from the inner barrel. FIG. 3A shows the wheel lock/clip 318 in a relaxed state. FIG. 3B shows the wheel lock/clip 318 in tension as applied to the wheel/wheel assembly 318.

FIG. 3B is a side view of a wheel assembly 318 with the wheel lock or clip 311 in an engaged position. Because FIG. 3B is a side view, inner barrel 66 is not visible in the drawing. In the compressed state (e.g., in tension), a force is applied toward the axis of the wheel 318 by a hinge that is formed by the arm 326 (the bent portion 331 and the extending portion 327) and the engagement tooth 319 in strain, pressing compressively toward the axis. Thus, the wheel lock/clip 311 is held in tension, thus causing the wheel/thumbwheel to be held in place by abutment or near abutment of an end 339 of the arcuate body and the housing 14 of the delivery device 10.

Figure 4B:
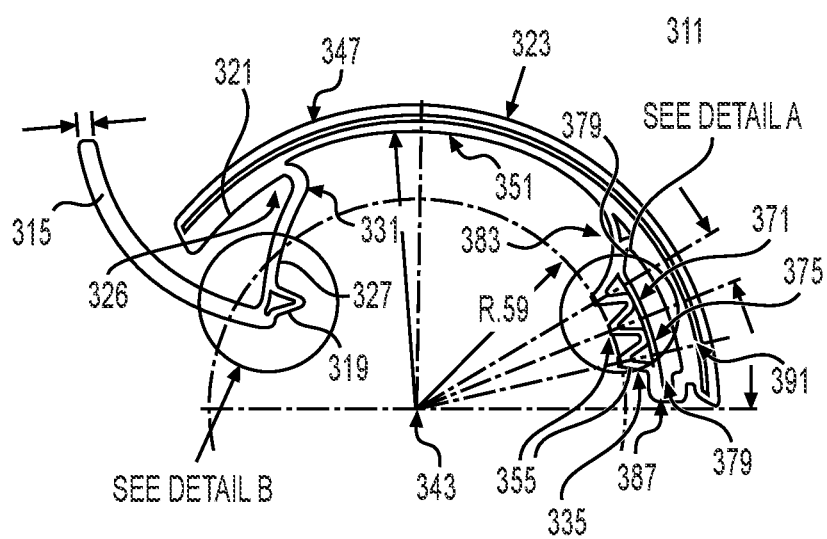
FIG. 4B is a side view of the wheel lock/clip of FIG. 4A in a disengaged state.
Figure 4C:
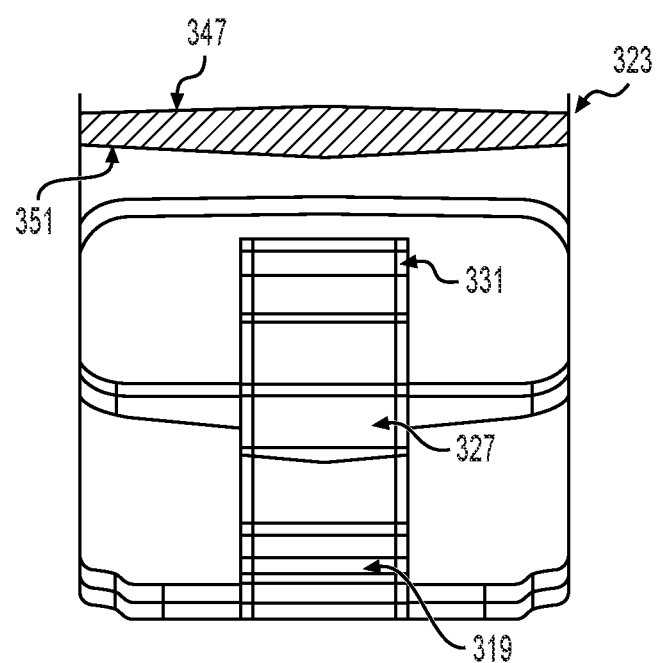
FIG. 4C is a front view of the wheel lock/clip of FIG. 4A in a disengaged state.

FIG. 4A is a perspective drawing of the wheel lock/clip 311 in a disengaged state. FIG. 4B is a side view of the wheel lock/clip 311 of FIG. 4A in a disengaged state. FIG. 4C is a front view of the wheel lock/clip 311 of FIG. 4A in a disengaged state. As illustrated in the figures, body 323 has a circular arc (is substantially curved in profile) to match a wheel to which it is to be applied. For example, the arc of the body 323 may have a radial center point 343 coincident with the wheel to which it is to be applied, although such is not required. Moreover, when applied to the wheel, the body 323 may be deformed to deform its shape while in tension. In the alternative, the body 323 in a relaxed state may not have an arc that matches the wheel, but may have an arc that substantially matches the wheel when applied to the wheel.

The body 323 may exhibit spring-like behavior such that arm 326 and the arc of the body 323 combine to create a spring that is energized or loaded when mounted to the wheel. Thus, the clip grabs the wheel (via the engagement tooth 319) in a way analogous to a contracting spring clamp. When the operator removes the piece by pulling the tab 315, he/she is momentarily straining the spring further by winding the spring at the location of the u-shape (bent portion 331) to release the engagement tooth 319 from the mating gear teeth (not shown) in the thumbwheel 318.

As shown in FIG. 4B, the body 323 has an upper surface 347 and a lower surface 351. Lower surface 351 should have an arc matched to the wheel to which the wheel lock is to be applied. Upper surface need not have an arced profile, although such arced profile is illustrated in the figures. Tab 315 is shown having a curved or arced profile, although tab 315 may be of any configuration that is greppable by a user to pull the tab away from the wheel with force enough to overcome the force supplied by the hinge formed by the bent portion 331 and the extending portion 327 to disengage the engagement tooth 319. The tab 315 may be flat or straight, may include a thumb or finger depression, may be textured or have any other configuration or shape to assist in gripping of the tab 315 by a user. Detail A of FIG. 4B is shown in FIG. 5A and Detail B of FIG. 4B is shown in FIG. 5B.

Figure 5A:
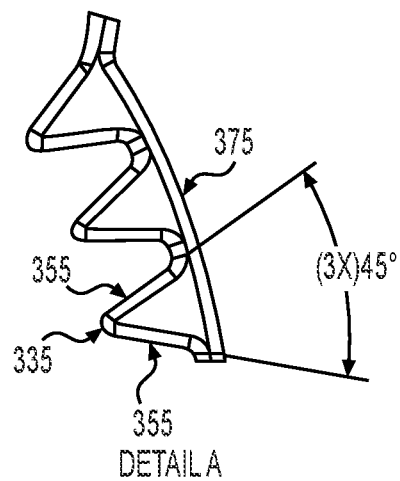
FIG. 5A illustrates features of detail A of FIG. 4B.

FIG. 5A illustrates additional teeth 335. As discussed above, three additional teeth 335 are shown for illustrative purposes. More or fewer additional teeth 335 may be provided within the scope of this disclosure. The teeth, as illustrated in FIG. 5A, are triangular in cross-section, with two struts 355 forming an angle of 45 degrees to form a vertex at the side of the tooth facing the wheel to be locked (not shown). As illustrated, each of the three additional teeth shown will have the same angle so as to properly engage with teeth on the inner barrel of inner barrel 66 (see FIG. 2). Vertices of the teeth lie on an arc sharing common radial center point 343 with each other and the wheel so as to engage the wheel (not shown) to which the wheel lock/clip is to be applied. While shown as comprising two struts, each additional tooth is not so limited and may be solid or a hollow structure and still be within the spirit and scope of the present disclosure. While illustrated here as having a triangular cross-section, the shape of the additional teeth is not so limited so long as the teeth are shaped to engage a complimentary structure on the wheel to which it is to be applied.

Referring to FIG. 4B, a brace arm 321 may lie adjacent the under surface 351 of the body and connect to hinge 331. As can be seen in FIG. 4B, the additional teeth 335 may be separated from the body 323 by a bridge structure 371. The bridge structure 371 may include a bridge strut 375 adjacent the under surface 351 of the body 323. The bridge strut 375 may be spaced apart from the under surface 351 of the body 323, extending from the body 323 and connected thereto by side struts 379. The bridge structure 371 itself may form a hinge compressible toward the body 323. The side struts 379 may be a living hinge such that force applied to the additional teeth cause the bridge to be compressible toward the body 323 when a force is applied to the additional teeth 335. In one aspect, the side struts 379 may connect to the bridge 375 such that points where a side strut 379 connects to the bridge is a hinge or living hinge. The additional teeth 335 may be attached to or merely adjacent the bridge structure 371 such that force applied to the additional teeth 335 causes deformation of the living hinge formed of the bridge structure 371. In addition, the additional teeth may extend from the body 323 via an additional tooth arm 383, which itself may be deformable/compressible toward the body 323 such that force applied to the additional teeth 335 causes deformation of the living hinge formed of the additional tooth arm 383. The additional teeth 335 may further connect to the body via a second additional tooth strut 385, which may be adjacent to or be the same as at least one of the side struts 379. The bridge structure 371 may further include a body strut 391 adjacent the body 323 such that the side struts 379 connect the body strut 391 to the bridge 375.

Figure 5B:
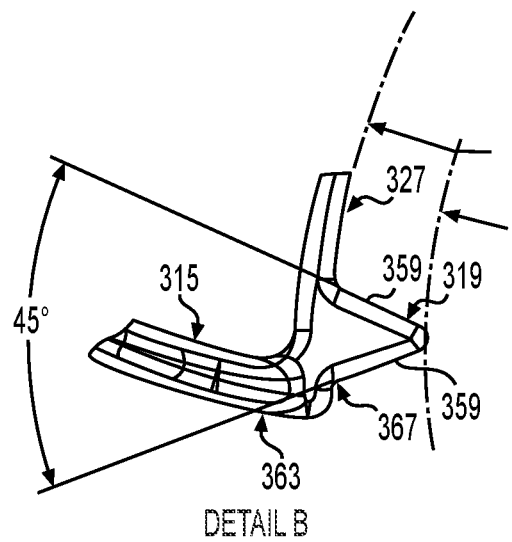
FIG. 5B illustrates features of detail B of FIG. 4B.

FIG. 5B illustrates engagement tooth 319 as it relates in the present embodiment to tab 315. The engagement tooth may be made of two struts 359 and have a triangular cross-section. While shown as comprising two struts, the engagement tooth is not so limited and may be solid or a hollow structure and still be within the spirit and scope of the present disclosure. While shown to be slightly offset along the arm 327 from a lower edge 363 of the tab 315, this is but one relationship of the engagement tooth 319 with respect to the tab 315. For example, an end 367 of a strut 359 of the engagement tooth 319 may align or be close to the lower edge 363 of tab 315. It is contemplated, though not necessary, for the end 367 to be curved or otherwise shaped to abut at least a portion an opposing vertex of a tooth (not shown) on the inner barrel 66. Also, arm 327 may have a circular arc such that when the wheel lock/clip 311 is engaged with the wheel to which it is applied the circular arc of the arm 327 shares the common radial center point 343 with the wheel. Similarly, when engaged with the wheel to which it is applied, a vertex of the engagement tooth lies on an arc sharing common radial center point 343 with each other and the wheel so as to engage the wheel (not shown) to which the wheel lock/clip 311 is to be applied.

Figure 6A:
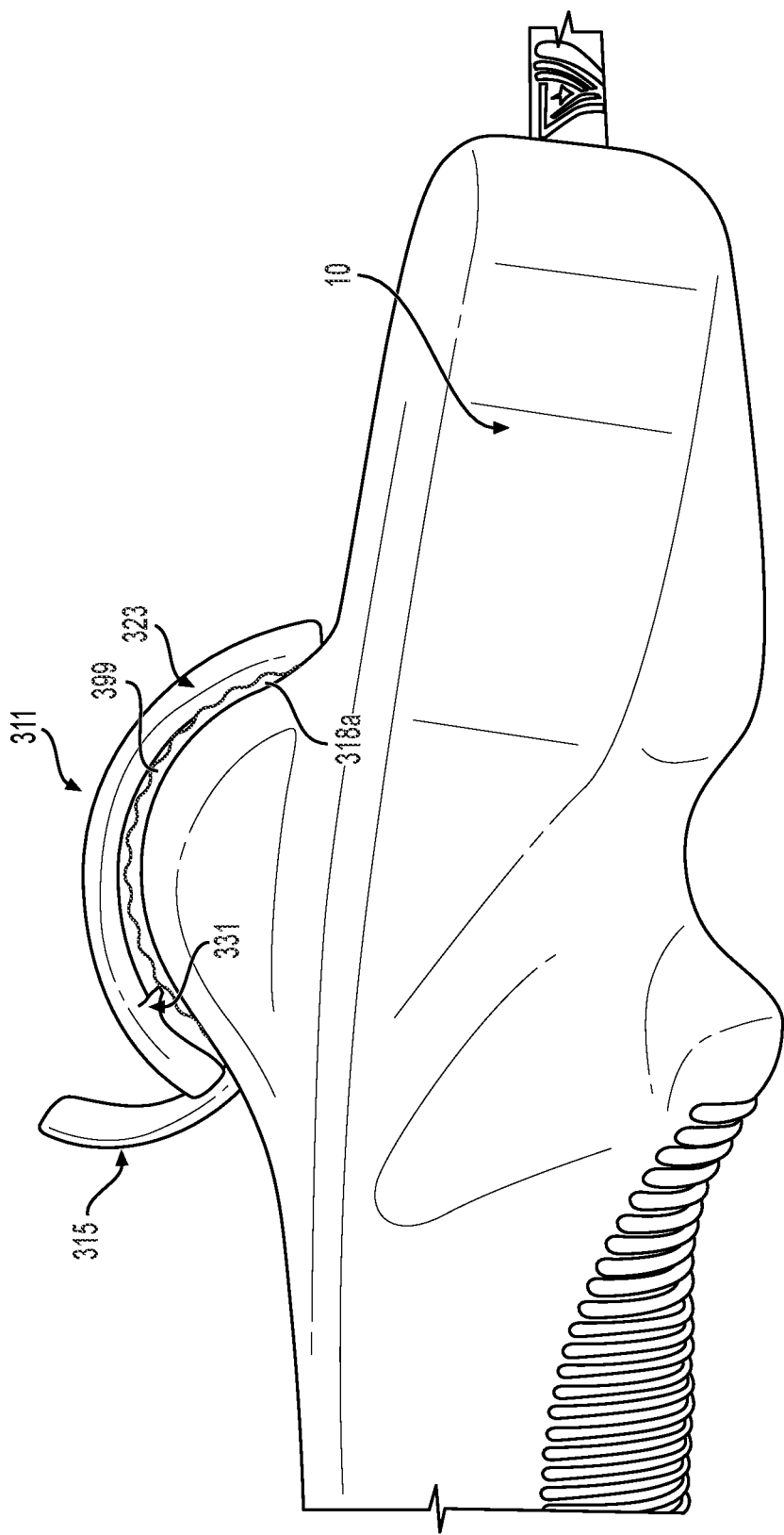
FIGS. 6A, 6B and 6C show a wheel lock/clip in accordance with principles described herein in place on an example thumbwheel actuated stent delivery device.
Figure 6B:
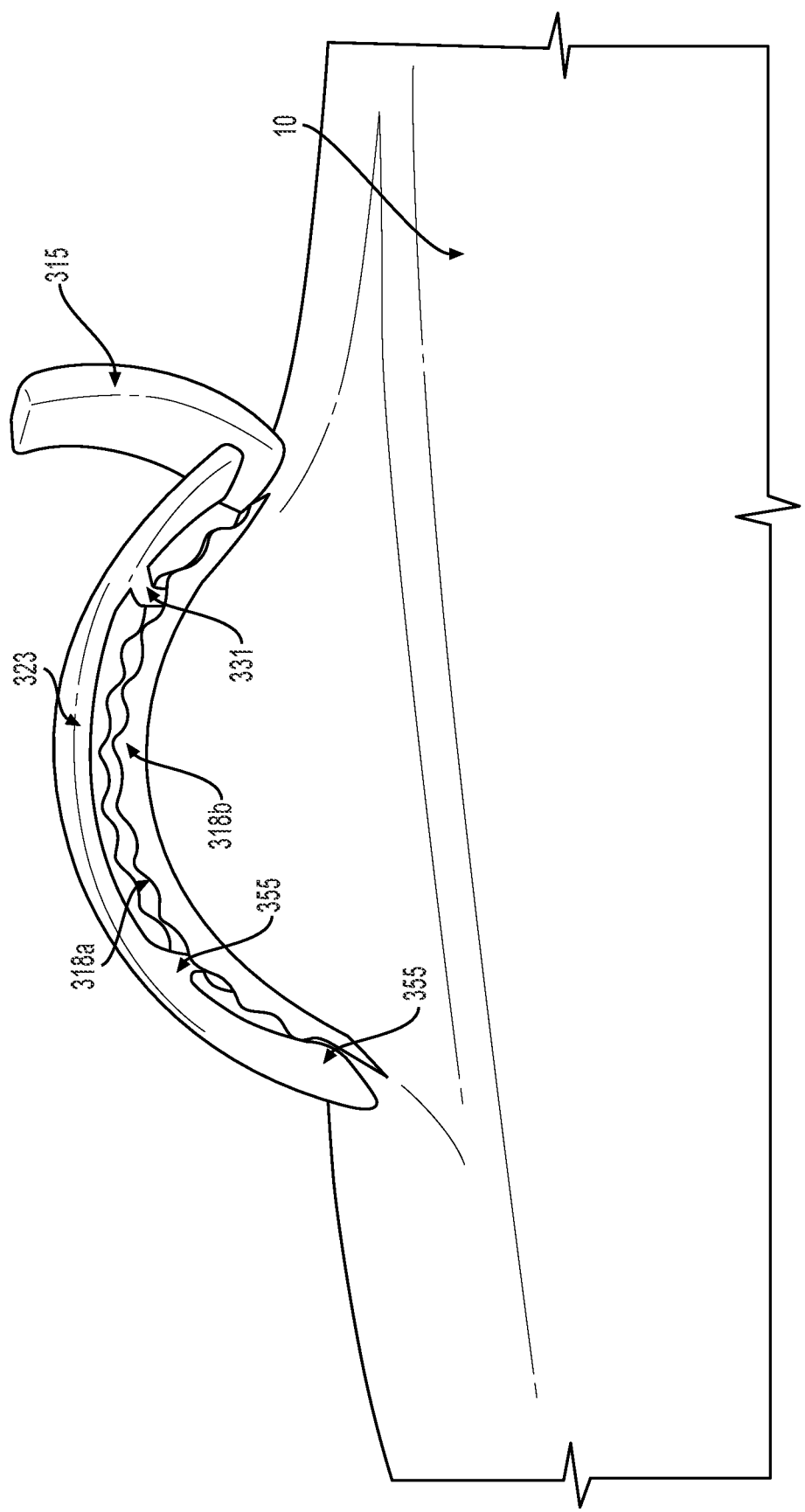
Figure 6C:
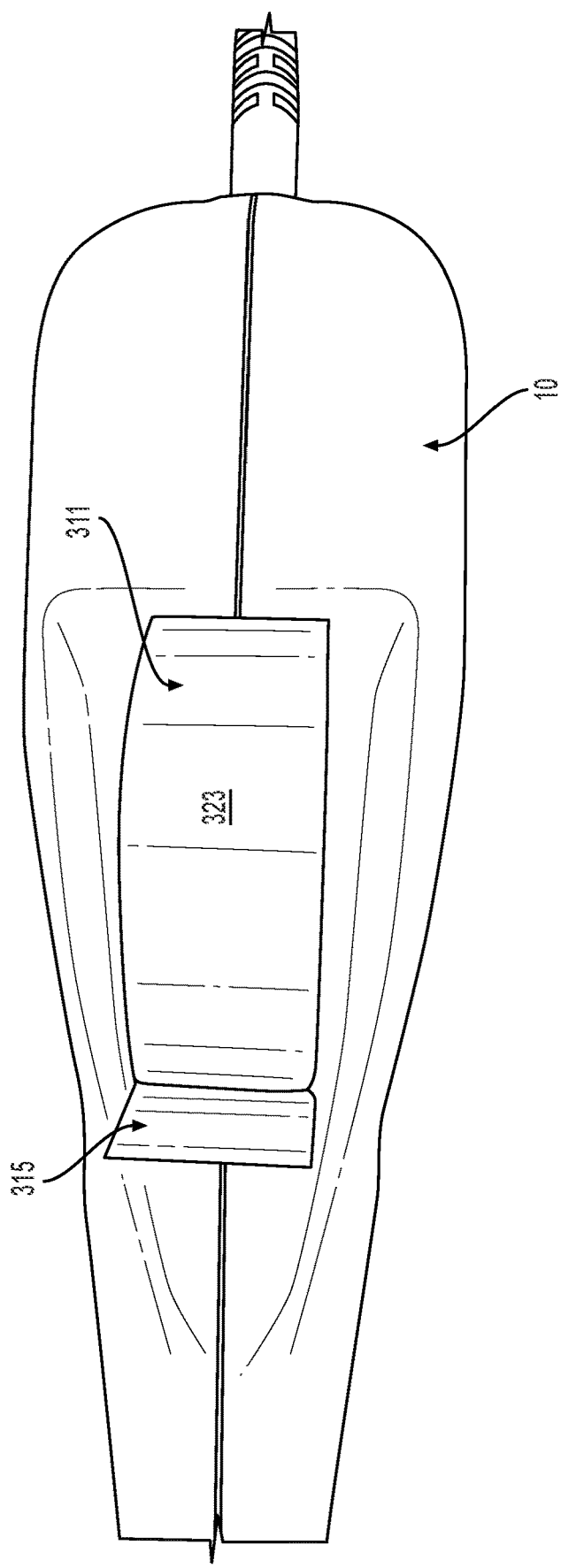
Figure 7:
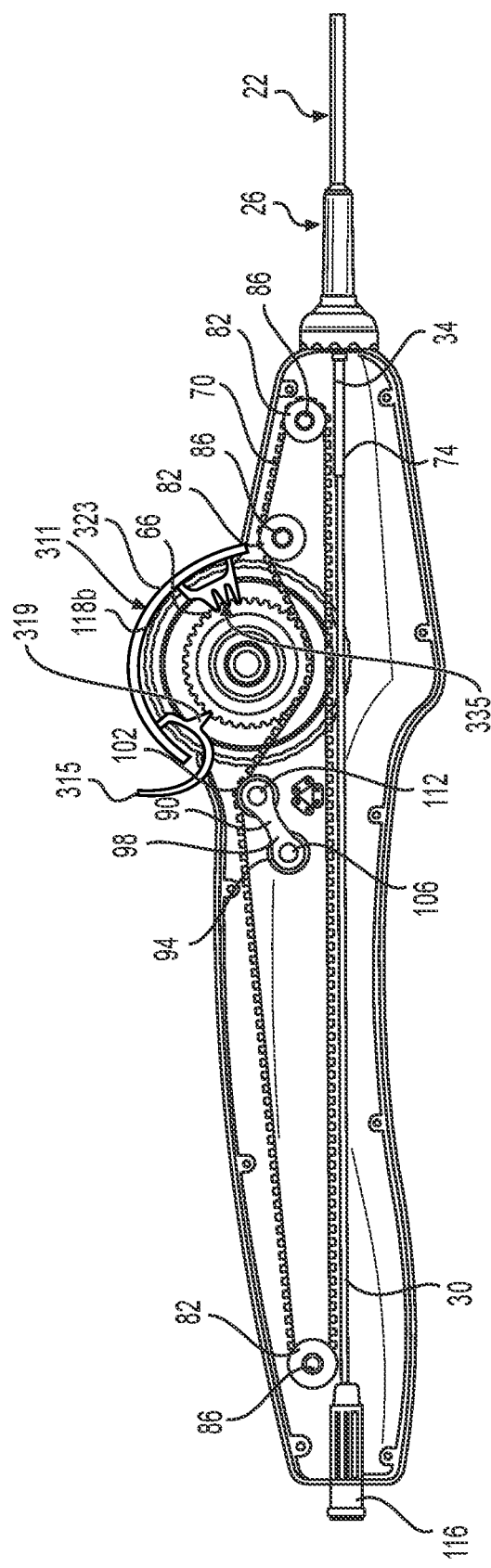
FIG. 7 is rough illustration wheel lock/clip engaged with an example thumbwheel actuated delivery system.
Figure 8:
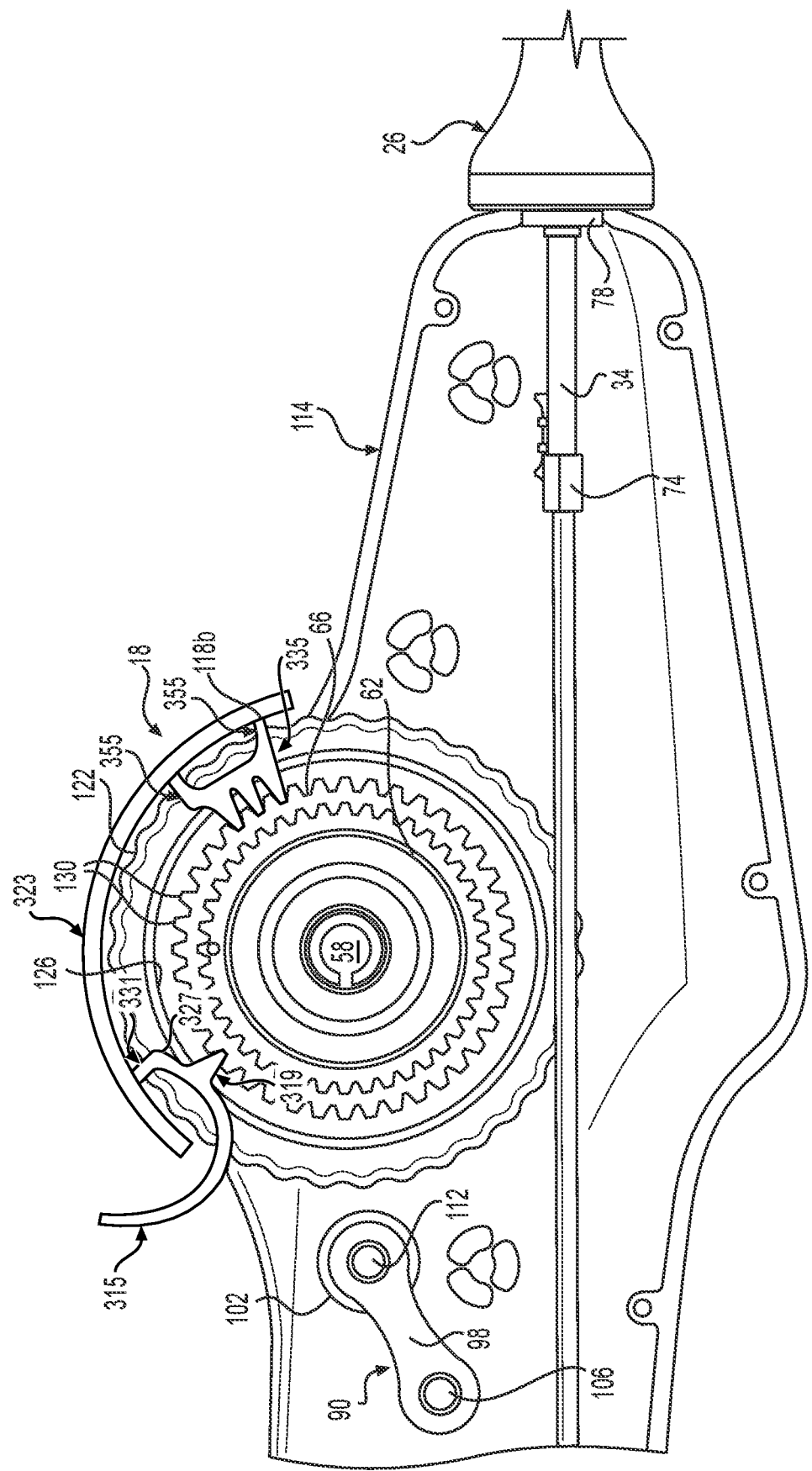
FIG. 8 is another rough illustration wheel lock/clip engaged with an example thumbwheel actuated delivery system.

FIGS. 6A, 6B and 6C show a wheel lock/clip 311 in accordance with principles described herein in place on an example thumbwheel actuated stent delivery device. As illustrated, the wheel lock/clip 311 is installed on the thumb-actuate wheel (not shown) with tab 315 to the posterior side of the thumbwheel. As such, and not shown, the engagement tooth engages a tooth on the inner barrel 66 (not shown) toward the posterior side of the thumbwheel. Looking closely at FIG. 6A, bent portion 331 can be seen in the space between the lower surface 351 of the body 323 and a thumb-contact surface 399 of the thumbwheel 318 (in this case 318a). Looking at FIG. 6B, struts 355 forming a side of a leading one of the additional teeth and a trailing one of the additional teeth can be seen in the space between the lower surface 351 of the body 323 and a thumb-contact surface 399 of the thumbwheel 318 (in this case 318b). FIGS. 7 and 8 are rough illustrations of how the wheel lock/clip 311 interacts/engages with a thumbwheel actuated delivery system of U.S. Pat. No. 10,449,073. The wheel lock/clip 311 prevents motion of the wheel by abutting a portion of the housing 14 of the wheel-actuated device 10 once installed.

The wheel lock/clip may be applied to the wheel of the delivery device but abutting additional teeth 335 in respective grooves between barrel teeth and using those teeth as a pivot point to then engage the engagement tooth 319 with a corresponding groove between barrel teeth. As shown the tab 315 faces the rear of the delivery handle, but such direction is not required. To disengage, a user pulls the tab 315, which causes the engagement tooth 319 to disengage from the corresponding groove, with the additional teeth being a pivot point and the last point of disengagement of the wheel lock/clip 311 from the inner barrel.

The wheel lock/clip 311 may be made of any deformable material capable of providing an appropriate higher flexural modulus and tensile properties. For example, although not limited thereto, nylon appropriate for health care application, such as Dupont Zytel® PA66, may be used to form the wheel lock/clip. Dupont Zytel® PA66 is generally unaffected by either EtO sterilization or gamma Nylon offers creep resistance properties and provides higher durability characteristics than some of the other choices, like acetal copolymer and ABS, although such materials can be used in place of nylon in the present design. Medical grade polycarbonate/ABS blend may also be used, for example, which include materials such as Covestro Bayblend®.

Although described with respect to application to an inner barrel structure, the wheel lock/clip described herein may be applied to any wheel with a toothed surface.

Figure 9:
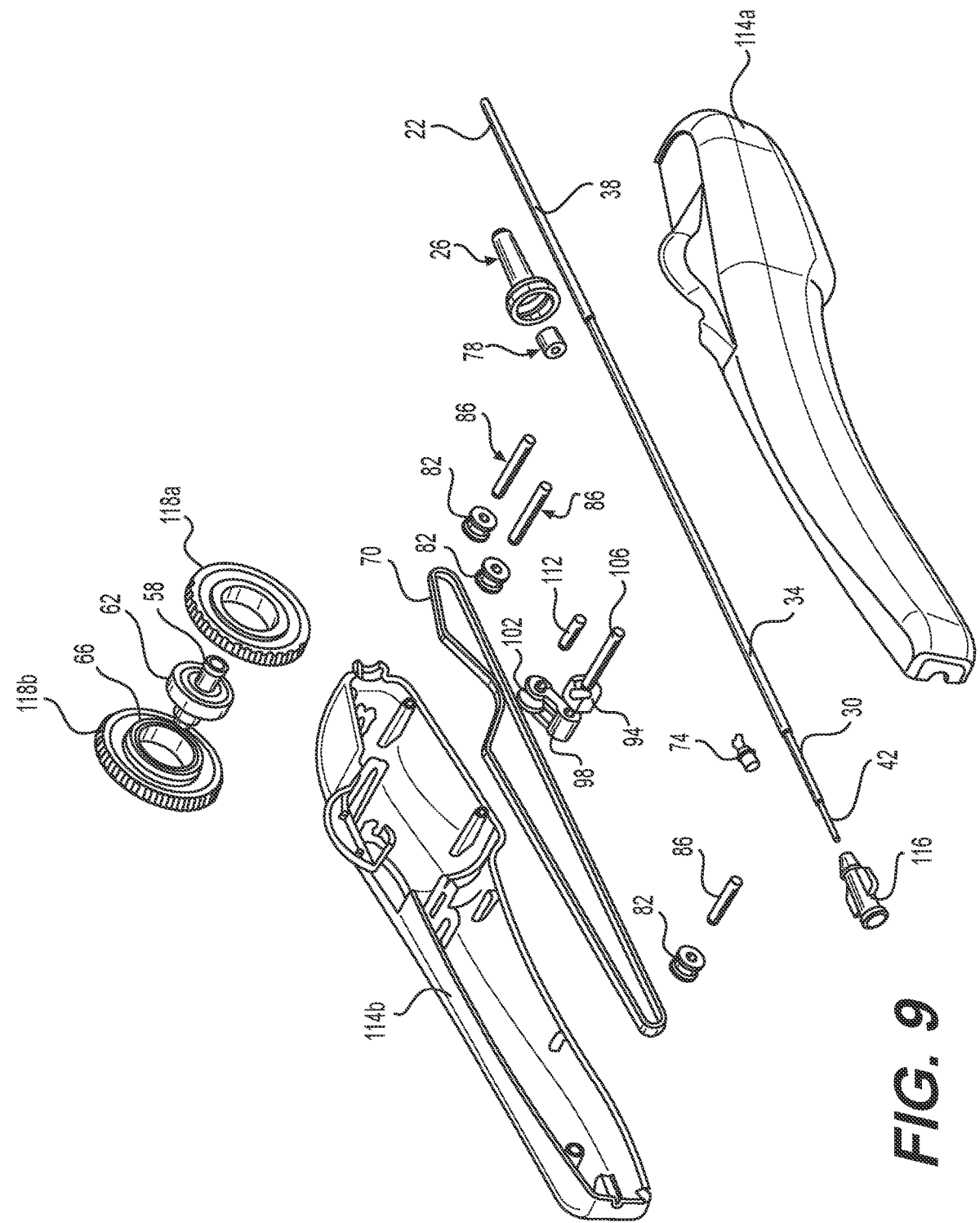
FIG. 9 illustrates is an exploded view of features of an example delivery handle.

FIG. 9 illustrates an exploded view of features of an example delivery handle to which the wheel lock/clip 311 may be applied for minimize rotation of a thumbwheel for shipping. The exemplary device illustrated in FIG. 9 includes a two-part housing 114a and 114b, where the respective two parts 114a and 114b may be snap fit together for assembly. The thumbwheel 18 may comprise two wheels 118a and 118b, an axle 58, and a bearing 62. The wheels 118a and 118b may include teeth on an inner barrel 66 thereof. Although only one inner barrel is shown in FIG. 9 on wheel 118b, wheel 118a may also include an inner barrel with teeth. The teeth on the inner barrel 66 are sized to correspond with teeth on a timing belt 70. A timing belt link 74 connects the outer sheath 34 to the timing belt 70. The housing may include a bushing 78, which may be a separate component or may be integral to the housing 14. The bushing may be formed of PEEK or other suitable material. The exemplary handle of FIG. 9 further includes at least one idler pulley 82 for tensioning and guiding the timing belt. Also shown in FIG. 9 idler pulley axles 86 corresponding to the idler pulleys 82 of the device of FIG. 9. The exemplary delivery handle of FIG. 9 further includes a tensioner assembly 90, the tensioner assembly 90 including a torsion spring 94, a tensioner arm 98, a tensioner pulley 102, a tensioner arm axle 106 and a tensioner pulley axle 112. In the presently described device, the timing belt has teeth on one side (outer diameter or periphery) of the belt and the inner diameter (inner surface) is smooth or substantially smooth or flat. The smooth or flat surface of the timing belt 70 contacts the idler pulleys 82 and the tensioner pulley 102.

In the exemplary device of FIG. 9, the outer support shaft 38 is fixed to the handle housing 14, and both the inner core 42 and outer sheath 34 are contained within the inner diameter of the outer shaft 38. The inner core 42 will be bonded at the proximal end along with a metal (e.g., stainless steel) shaft 30 to a female luer 116, which is coupled to or clamped into the handle body 14. In an aspect of the present invention, the metal shaft 30 may be bonded to the outer diameter of the inner core 42 to provide support/rigidity at the proximal end where the inner core 42 is unsupported in the handle body 10. The support of the metal shaft 30 over the inner core 42 mitigates potential deformation/buckling of proximal unsupported inner core 42 during stent deployment. As the outer sheath 34 is pulled back to release/deploy the stent, the inner core 42 is put into compression, therefore the unsupported proximal end of the inner core could deform. The bonded metal shaft 30 provides support and column strength to unsupported proximal inner core 42. The metal shaft 30 may be sized such that is slides over the outer diameter of the inner core 42 and through the inner diameter of the outer sheath 34. The metal shaft 30 does not impact the inner diameter of the inner core 42, so a guidewire (not shown) can still pass through entire assembly. A material other than metal may be used to for the support shaft, and the invention described herein is not limited to metal for use in the support shaft 30.

The outer sheath 34 is coupled to or bonded to the timing belt link 74 to deliver the stent by retracting the outer sheath 34 by movement of the thumbwheel, which in turn engages the teeth of the timing belt 70 via the inner barrel 66 and the teeth on the inner barrel 66. The metal shaft 30 that is coupled to or bonded to the inner core 42/female luer 116 is a guide rail that the outer sheath 34 and timing belt link 74 move proximally over during deployment.

Figure 10:
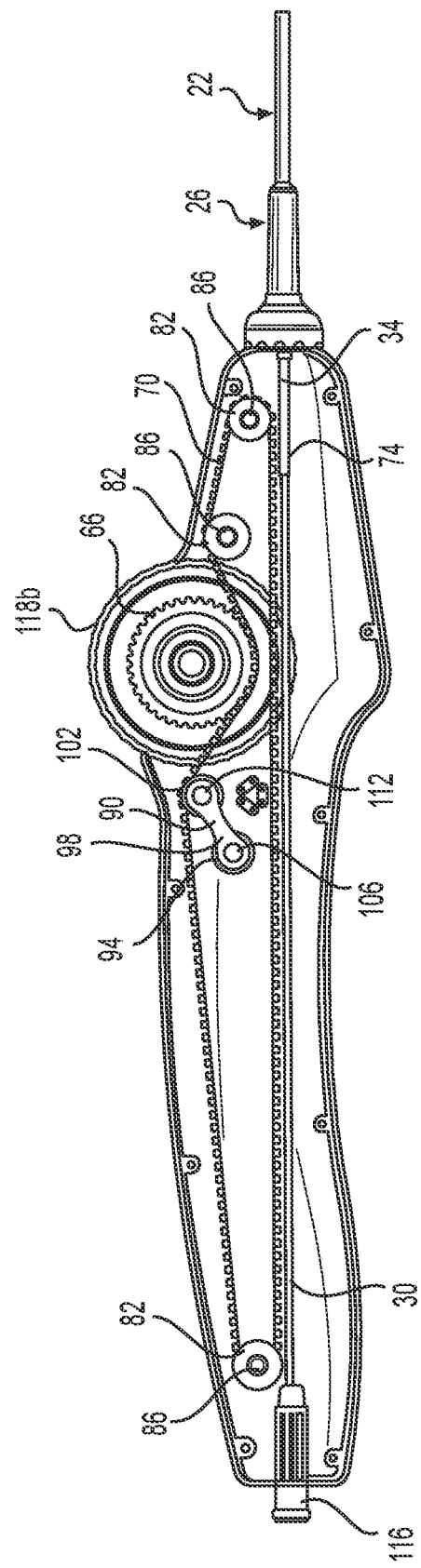
FIG. 10 is cross-sectional view of an assembled example delivery handle.

FIG. 10 is a cross-sectional view of an assembled example delivery handle. The exemplary device illustrated in FIG. 10 shows one part 114b of the two-part housing, where the respective two parts may be snap fit together for assembly. Other assembly methods may be used to mate the two parts together such as welding, bonding, gluing or other method. It is contemplated that each side of the two part housing is symmetrical and complementary, but such configuration is not required. The parts of the thumbwheel assembly 18 may be formed by molding, such as injection molding. The housing 14 may be unitary.

FIG. 10 illustrates one wheel of the thumbwheel assembly 18 that may comprise two wheels 118a and 118b, an axle 58, and a bearing 62. The bearing may include a ball bearing with an inner and outer grooved bearing race. The bearing serves to reduce rotational friction between the thumbwheel and the axle and may be eliminated if the frictional forces are acceptable. An acetal bushing or other method of friction reduction may be used in place of the bearing 62.

The wheels 118a and 118b may include teeth on an inner barrel 66 thereof. Although only one inner barrel is shown in FIG. 10 on wheel 118b, wheel 118a may also include an inner barrel with teeth. The teeth on the inner barrel 66 are sized to correspond with a timing belt 70. The inner barrel may be formed by molding, such as injection molding, and the teeth may be formed as part of the molding or other method such that the teeth are integral to the inner barrel 66. In another aspect, the teeth may be separable from the inner barrel 66.

As shown, the timing belt link 74 connects the outer sheath 34 to the timing belt 70. The exemplary handle of FIG. 10 further includes at least one idler pulley 82 for tensioning and guiding the timing belt 74. Also shown in FIG. 10 idler pulley axles 86 corresponding to the idler pulleys 82 of the device of FIG. 10. The exemplary delivery handle of FIG. 10 further includes a tensioner assembly 90, the tensioner assembly 90 including a torsion spring 94, a tensioner arm 98, a tensioner pulley 102, a tensioner arm axle 106 and a tensioner pulley axle 112. In the exemplary device of FIG. 10, the outer support shaft 38 is fixed to the handle housing 14, and both the inner core 42 and outer sheath 34 are contained within the inner diameter of the outer shaft 38. The inner core 42 will be bonded at the proximal end along with a metal (e.g., stainless steel) shaft 30 to a female luer 116, which is coupled to or clamped into the handle body 14.

Figure 11:
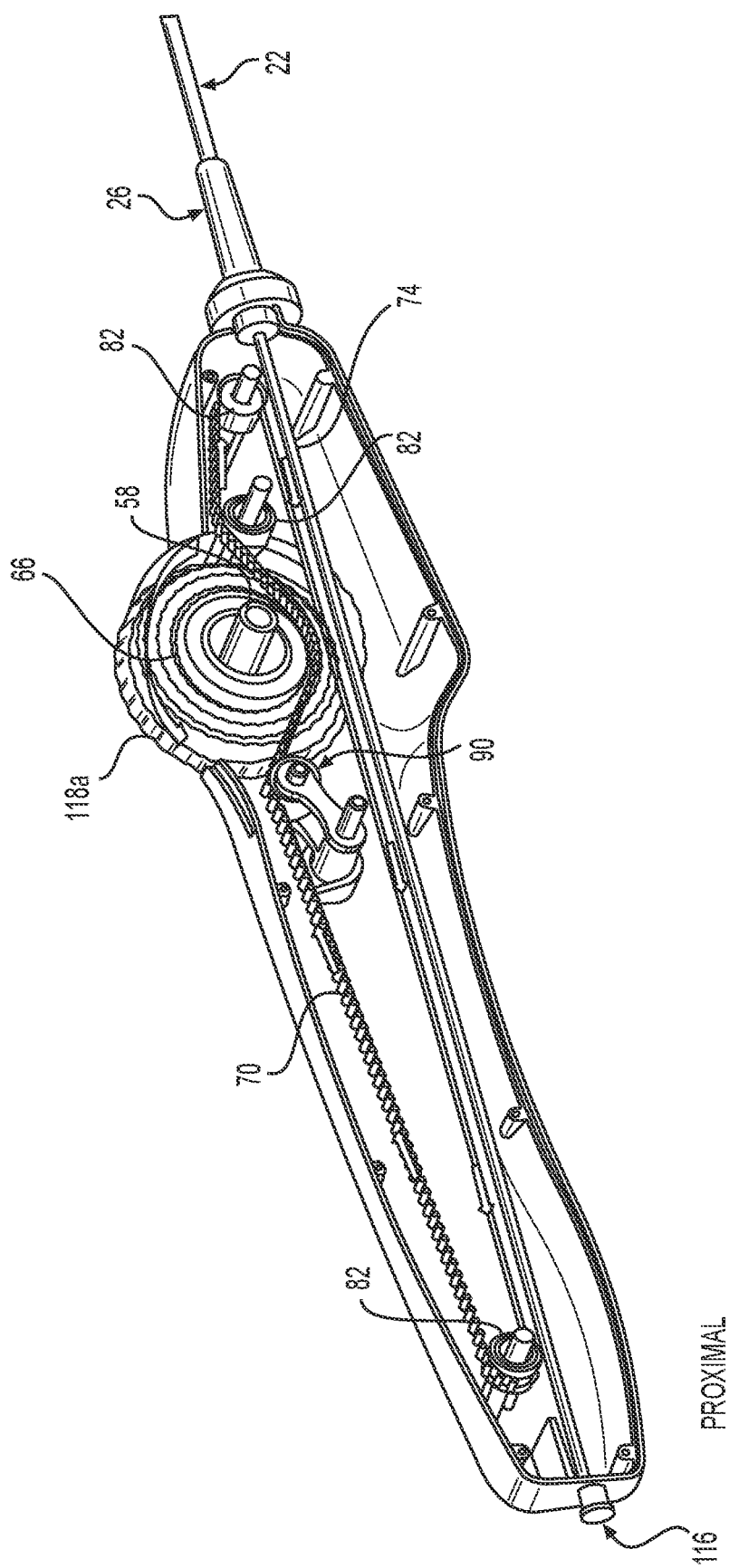
FIG. 11 is a cross-sectional view illustrating motion of the example thumbwheel and the timing belt.

FIG. 11 further illustrates motion of the thumbwheel 18, timing belt 70 and timing belt link 74 for deployment of a stent. As illustrated in FIG. 11, outer sheath 34 is translated proximally over guide tube/inner core 42 by the timing belt 70 by rotating the thumbwheel in the direction of the arrow. The timing belt 70 is driven by an operator via dual thumbwheel assembly 18, which may comprise integrally molded gear teeth, the pitch and shape of which correspond to teeth of the timing belt 70 for synchronizing/engaging the timing belt and causing movement of the timing belt to cause movement of the timing belt link, which is coupled to the outer sheath 34 to cause movement thereof for unsheathing (deploying) a stent provided therein. The diameter of the inner barrel 66, number of teeth on timing belt 70, and the pitch/frequency of the teeth on the timing belt 70 may each be adjusted/modified to allow for variable mechanical advantage during stent deployment and variable translation ratio. In addition, variable speed delivery may also be achieved by actuating the thumbwheel assembly 18 at the desired speed.

In the device illustrated in FIG. 11, rotation of the portion thumbwheel 18 external to the handle proximally (in the direction of the arrow) causes an upper portion of the portion of the timing belt adjacent the portion of the thumbwheel internal to the handle to move distally (in the direction of the arrow). The timing belt 70 extends around an idler pulley 82 such that a portion of the timing belt 70 adjacent the timing belt link 74 move proximally (in the direction of the arrow), engaging the timing belt link 74 to move the timing belt link 74 proximally, which moves the outer sheath 34 coupled thereto proximally, thereby unsheathing the stent for deployment. Movement may be reversed for re-sheathing of catheter following stent deployment.

Figure 12A:
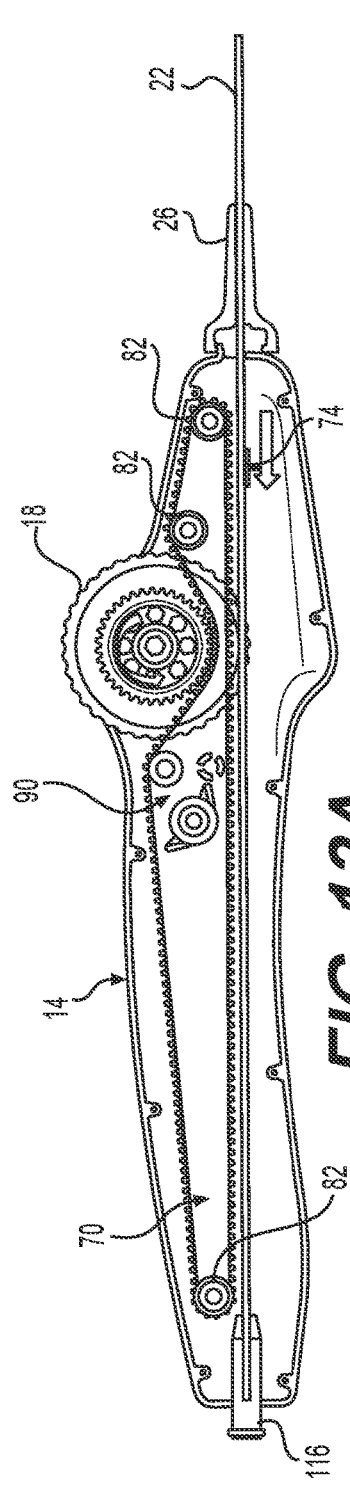
FIGS. 12A, 12B and 12C are cross-sectional views of the example delivery device illustrating motion of the timing belt link and outer sheath upon movement of the thumbwheel.
Figure 12B:
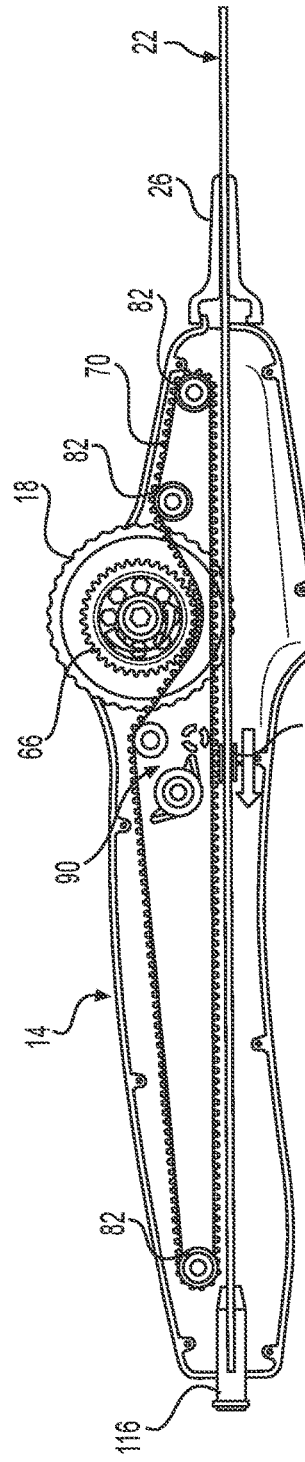
Figure 12C:
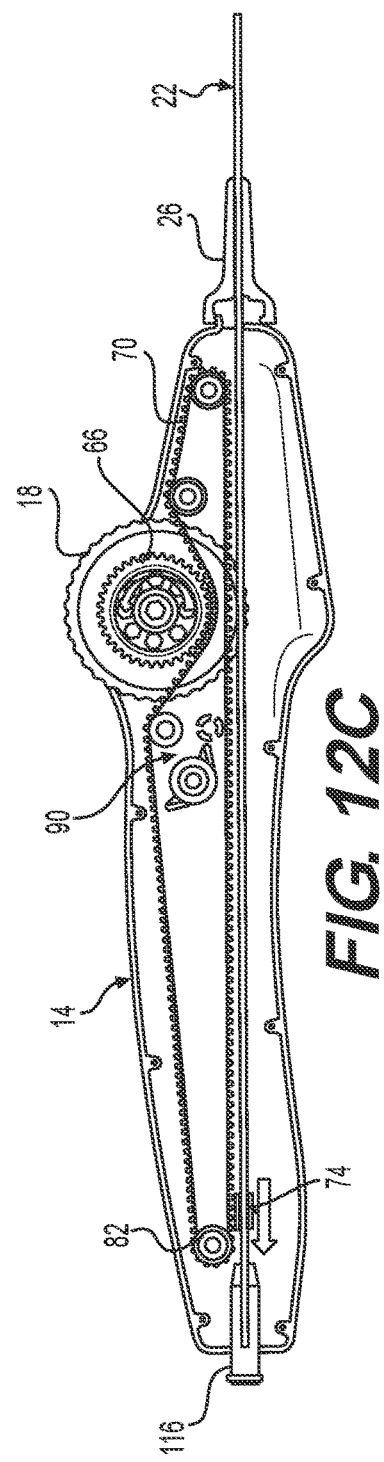

FIGS. 12A, 12B and 12C are cross-sectional views of the example delivery device illustrating motion of the timing belt link 74 and outer sheath 34 upon movement of the thumbwheel 18 counterclockwise in the context of FIGS. 12 A. 12B and 12C. It should be appreciated that the direction of thumbwheel rotation described herein is described in the context of the cross-section provide, but that it is contemplated that the portion of thumbwheel external to the handle 14 will be rotated rearward (in a proximal direction). It is also contemplated that the configuration of the timing belt 70 may be adjusted (for example, looped over the thumbwheel) to modify the direction of rotation of the thumbwheel corresponding to the proximal movement (retraction) of the outer sheath 34.

As shown in FIG. 12A, in an introducing position, the timing belt link is at a distal end of the handle housing. As the thumbwheel 18 is actuated in a predetermined direction, e.g. in the context of the cross-section shown, counterclockwise, the timing belt link/shuttle 74 moves proximally. Because the timing belt link/shuttle 74 is coupled to the outer sheath 34, the outer sheath moves proximally with the timing belt link/shuttle to expose a stent or other medical device mounted on the inner core 42 (not shown). FIG. 12B illustrates the positioning of the timing belt link/shuttle in a partially deployed position (e.g. the stent is partially deployed (not shown)). As the thumbwheel 18 is further rotated in a timing belt link/shuttle 74 further translates proximally to allow for full deployment of the stent or medical devices from the of the inner core 42, as shown in FIG. 12C. In the device here described, the thumbwheel 18 is actuated such that the upper side (external portion) of the thumbwheel is rotated proximally to cause the timing belt link/shuttle 74 to transit proximally. It is appreciated that the configuration/path of the timing belt 70 may be configured such that a distal rotation of the upper side (external portion) of the thumbwheel 18 may cause the timing belt link/shuttle 74 to transit proximally to cause the outer sheath 34 to retract from the inner core 42 to allow deployment of the medical device (not shown).

Figure 13:
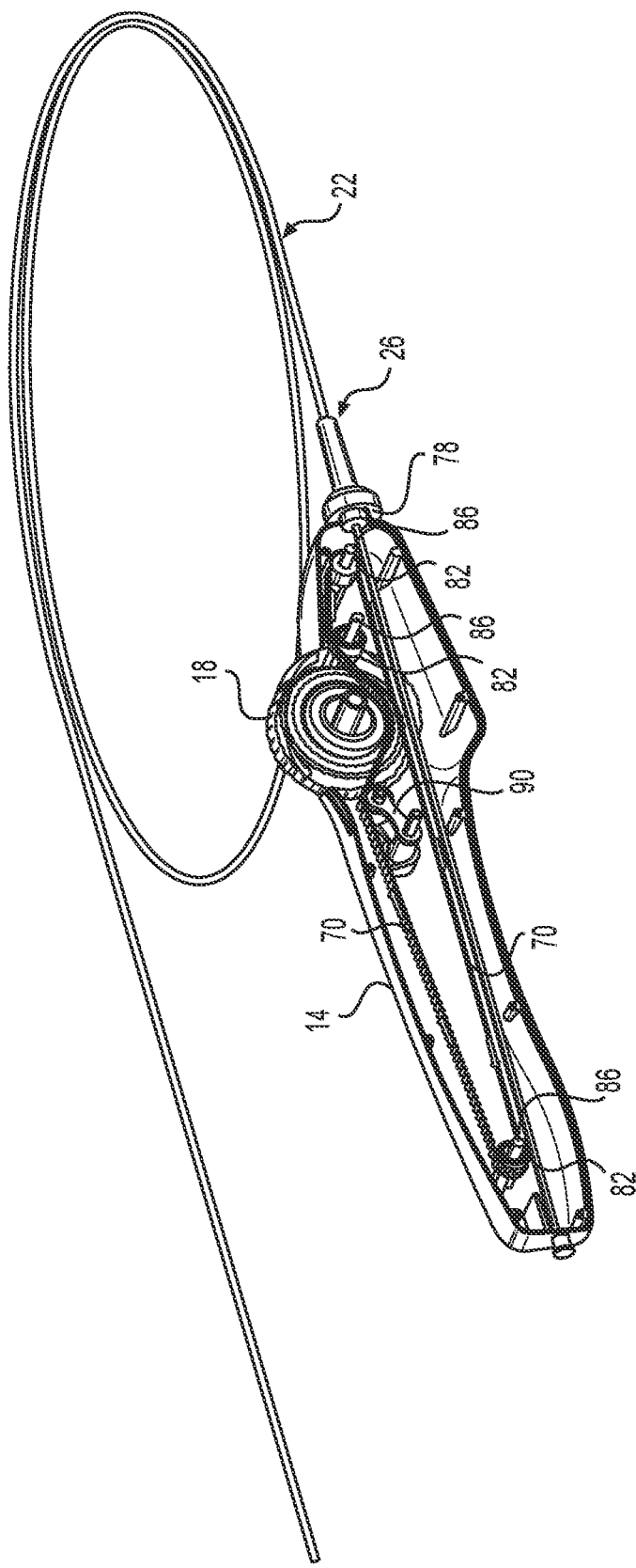
FIG. 13 illustrates a perspective view of the example delivery device, including a delivery catheter device.
Figure 23A:
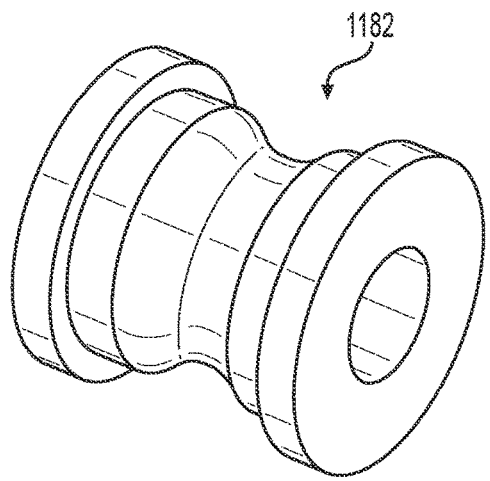
FIGS. 23A and 23B illustrates an example idler that may be used with the posi-drive belt illustrated in FIG. 22.
Figure 23B:
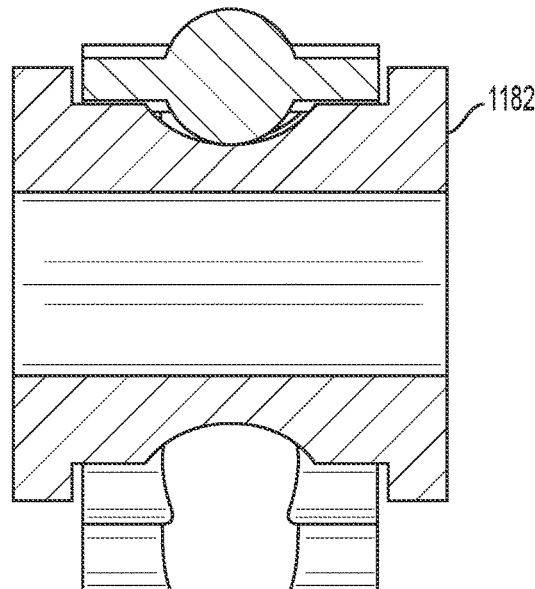

FIG. 13 illustrates a perspective view of the example delivery device, including the catheter device. As shown in FIG. 13, the timing belt 70 extends around idler pulleys 82 and the tensioner pulley 102 of tensioner 90. The tensioner pulley 102 is coupled to the torsion spring 94 via the tensioner arm 98. Tension is maintained on the timing belt by torsion spring 94 on tensioner arm axle 106, which urges the tensioner pulley 102 into contact with the timing belt 70 via the tensioner arm 98. An example idler pulley 82 is illustrated in FIGS. 23A and 23B.

Figure 14:
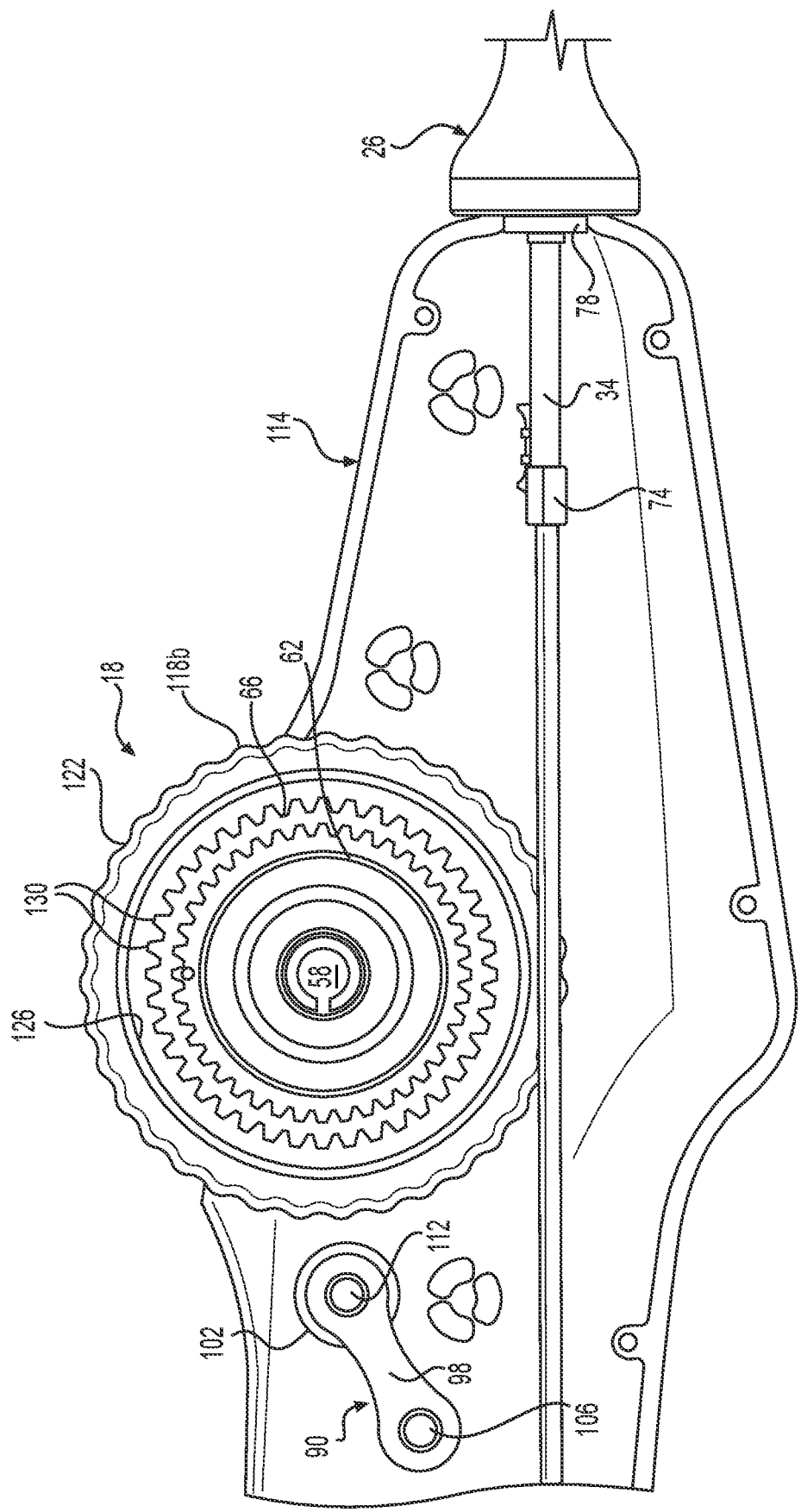
FIG. 14 is a cross-sectional line drawing showing detail of an example thumbwheel assembly.

FIG. 14 is a cross-sectional line drawing showing detail of an example thumbwheel assembly 18 and the timing belt link 74. As illustrated in FIG. 14, one part 118b of a two-part thumbwheel 18 has an outer surface 122 that may be textured for ease of use. The thumbwheel part 118b may also include an inner surface or rim 126. An inner barrel 66 extends from the thumbwheel part 118b and has a plurality of barrel teeth 130 thereon. The barrel teeth 130 on the inner barrel 66 are sized to correspond with a timing belt (not shown). Although not illustrated, the barrel teeth 130 may have a standard periodicity (pitch) or may have a variable periodicity (pitch) such that actuation of the thumbwheel assembly may cause movement of the timing belt (not shown) and thus translation of outer sheath 34 at a first rate when barrel teeth of a first periodicity engage the timing belt (not shown) and at a second rate when barrel teeth of a second periodicity engage the timing belt (not shown). Such variable rate may be imparted by having different spacing/periodicity/pitch of the teeth on the timing belt instead of or in addition to having different spacing/periodicity/pitch of the barrel teeth 130 on the inner barrel 66. FIG. 14 further illustrates the thumbwheel bearing 62 and the thumbwheel axle 58.

A safety locking feature (not shown) may be incorporated in the handle design such to mitigate inadvertent actuation of the handle during transit and storage. The safety locking feature may be a removal/disposal or toggle feature that engages the teeth on the inner barrel to lock it in place and prevent rotation. The safety locking feature may also be a feature that engages the timing belt link to prevent its translation.

Figure 15:
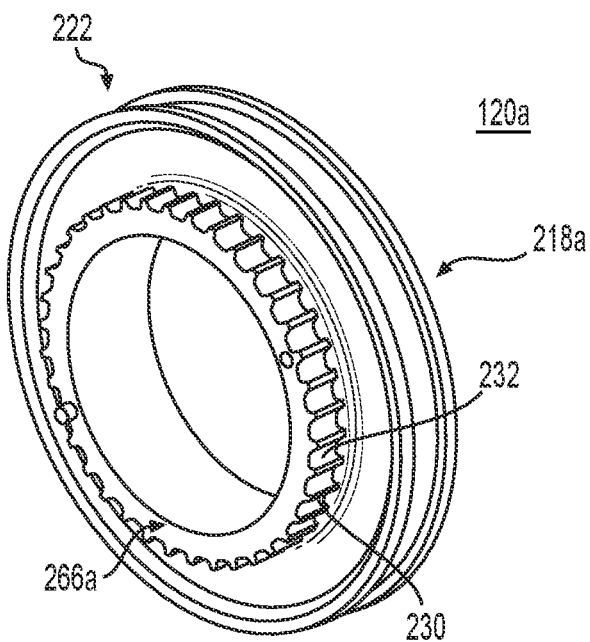
FIG. 15 illustrates a portion of the example thumbwheel.

FIG. 15 illustrates a portion of an example thumbwheel. The thumbwheel may comprise two wheel parts 120a and 120b, as shown in at least FIG. 3. As illustrated in FIG. 15, one of the wheel parts 120a may be a body 222 including a portion of the thumbwheel 218a (e.g. the outer circumference a portion of which extends through the housing such that a user can rotate the thumbwheel to actuate the device) and a portion of the barrel 266a (e.g. a portion of which engages the timing belt (not shown) to move the timing belt). The wheel part 120a may be unitary such that the thumbwheel portion 218a that extends through the housing and the barrel portion 266a may be unitary (e.g., they can be formed in a single molding process). The other wheel (not shown) may also include both a portion of the thumbwheel for actuation and a portion of the barrel such that the two "wheels" may be fit together to form the thumbwheel and barrel assembly. In other words, the other wheel may be a mirror image of the wheel described above. In some configurations, the two "wheels" may be the same, such that only one mold may be used. It is also possible that the thumbwheel assembly is formed as a single unit to include both the barrel and the thumbwheel portions.

Figure 16:
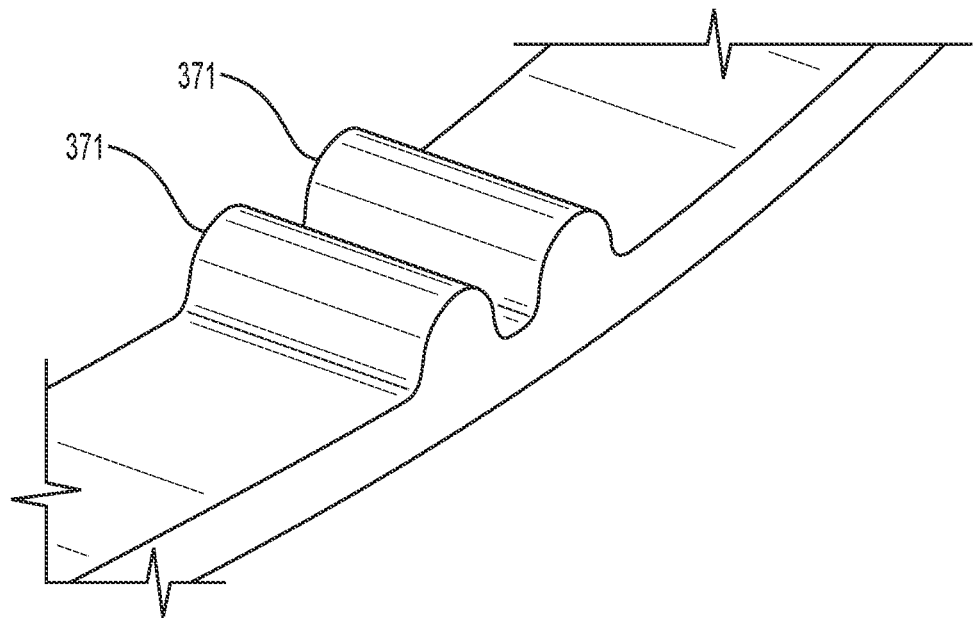
FIG. 16 illustrates exemplary belt teeth.

As shown in the exemplary device of FIG. 15, the exemplary wheel part barrel portion 266a includes grooves 232 that are substantially equally/evenly spaced to engage the pitch of a corresponding timing belt (not shown). The timing belt includes a plurality of substantially equally/evenly spaced teeth along a face of the belt to engage the grooves 232 on the corresponding barrel 266. FIG. 16 illustrates exemplary belt teeth. The belt shown in FIG. 16 is exemplary only, as it only shows two teeth, but the belt is designed to have teeth along enough of the belt to sufficiently deploy the stent.

Figure 17:
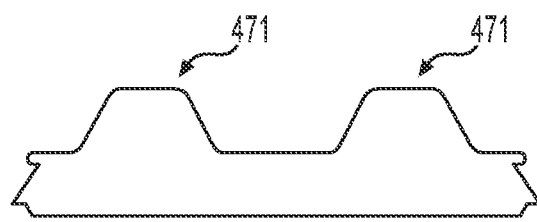
FIG. 17 illustrates exemplary belt teeth.

Other exemplary belt teeth are shown in FIG. 17. As illustrated in FIG. 17, exemplary belt teeth 471 may have a tapered shape with a flat top, e.g., trapezoidal cross-section, to allow for engagement with the barrel teeth 230 or groove 232. Although a trapezoidal cross section is shown, the teeth are not so limited and may be of any cross section that may engage with the barrel teeth sufficiently to allow belt movement to be actuated by barrel rotation. Other possible shapes, without limitation, include; without limitation, include circular, cylindrical, diamond, square, triangular or any variation thereof.

Figure 18:
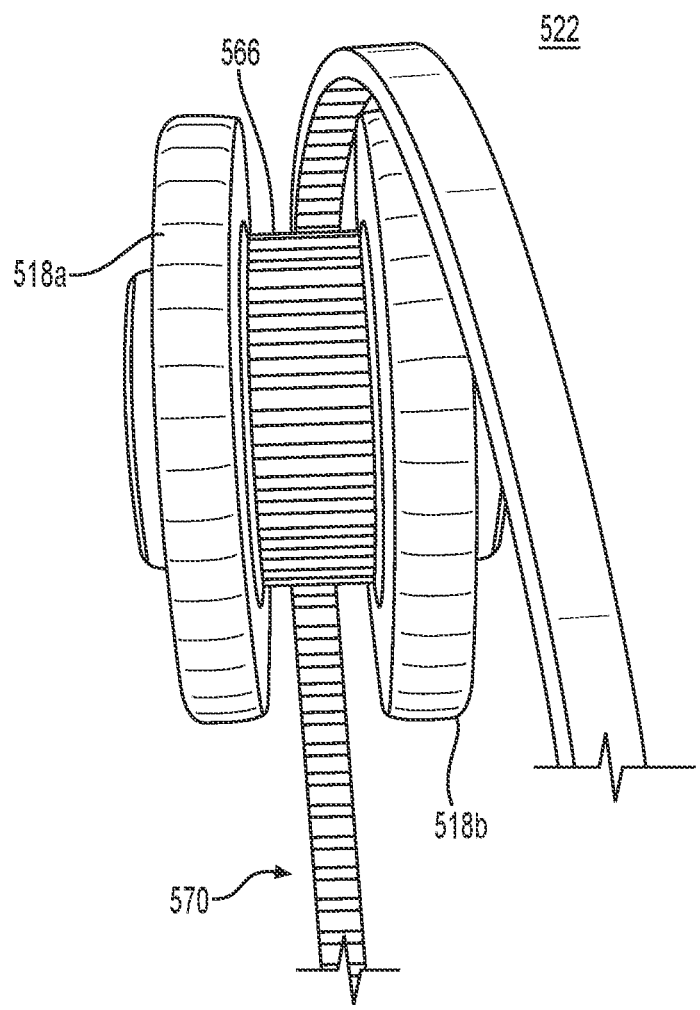
FIG. 18 shows an examplethumbwheel/barrel assembly with a timing belt.

In some cases, the timing belt may be looped over the barrel of the thumbwheel to provide more full engagement of the timing belt with the barrel. In this device, a longer timing belt would be used such approximately 360 degrees of engagement may be achieved between the belt and the barrel. FIG. 18 shows a prototype thumbwheel/barrel assembly 522 with a timing belt 570 where the barrel width is sized to allow for the timing belt 570 shown to be looped around the barrel 566 at least one full revolution. For example, cylindrical surface of the barrel 566 with the teeth could be sized to be twice the width of the timing belt 570 to accommodate the timing belt 570 being looped over the barrel 566 twice. The widened barrel 566 might thus have that the two parts of the thumbwheel 518a and 518b be spaced further apart than if the timing belt only engaged the barrel 566 at a fraction of the circumference of the barrel 566. In one aspect, the thumbwheel outer cylindrical edge could be modified to cause some over the outer edge of each portion of the thumbwheel to "overhang" the barrel to allow a more surface area for user engagement.

In another aspect, the barrel may be substantially cylindrical, such that an end of the cylinder has a set of teeth and/or grooves and the other end of the cylinder has a set of teeth and/or grooves. The barrel may further comprise a core region between the ends having teeth and/or grooves. The barrel with such teeth may be a unitary piece or may be two parts that are fitted together. The ends of the substantially cylindrical barrel are spaced apart sufficient to receive a central portion of a belt therebetween. A timing belt for use with the barrel thus described has a plurality of protrusions on opposite sides of the belt, for example, extending perpendicular to a pitch axis of the belt. The protrusions are designed to engage corresponding teeth and/or grooves on the barrel to transfer torque from the barrel to the belt, which is coupled to the outer sheath as described above, to cause deployment of the stent. The barrel may further comprise a groove therein for receiving a portion of the belt, such that the barrel itself may not be substantially cylindrical.

The barrel assembly may be formed by placing two disks with appropriately spaced teeth on circumferential edge thereof a distance apart sufficient to allow teeth on each of the disks to engage teeth of the timing belt. A cylindrical core may extend between each of the disks. The cylindrical core and "disks" may actually be a unitary piece that is substantially cylindrical, such that an end of the cylinder has a set of teeth and/or grooves and the other end of the cylinder has a set of teeth and/or grooves with a core region therebetween. The teeth and/or grooves on the two ends may be substantially aligned.

Figure 19:
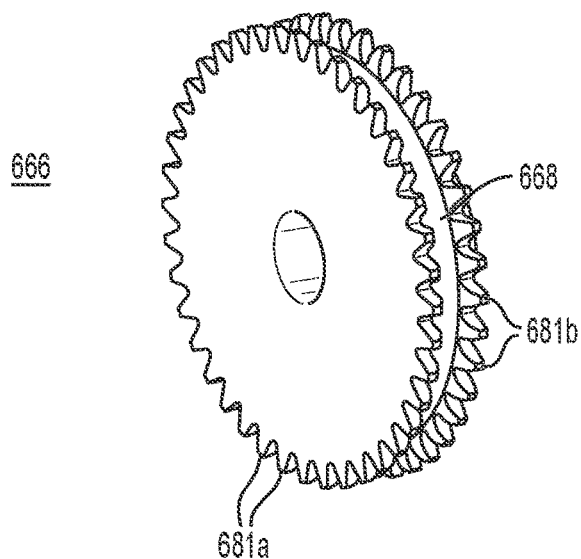
FIG. 19 illustrates an example barrel having two sets of teeth.
Figure 20:
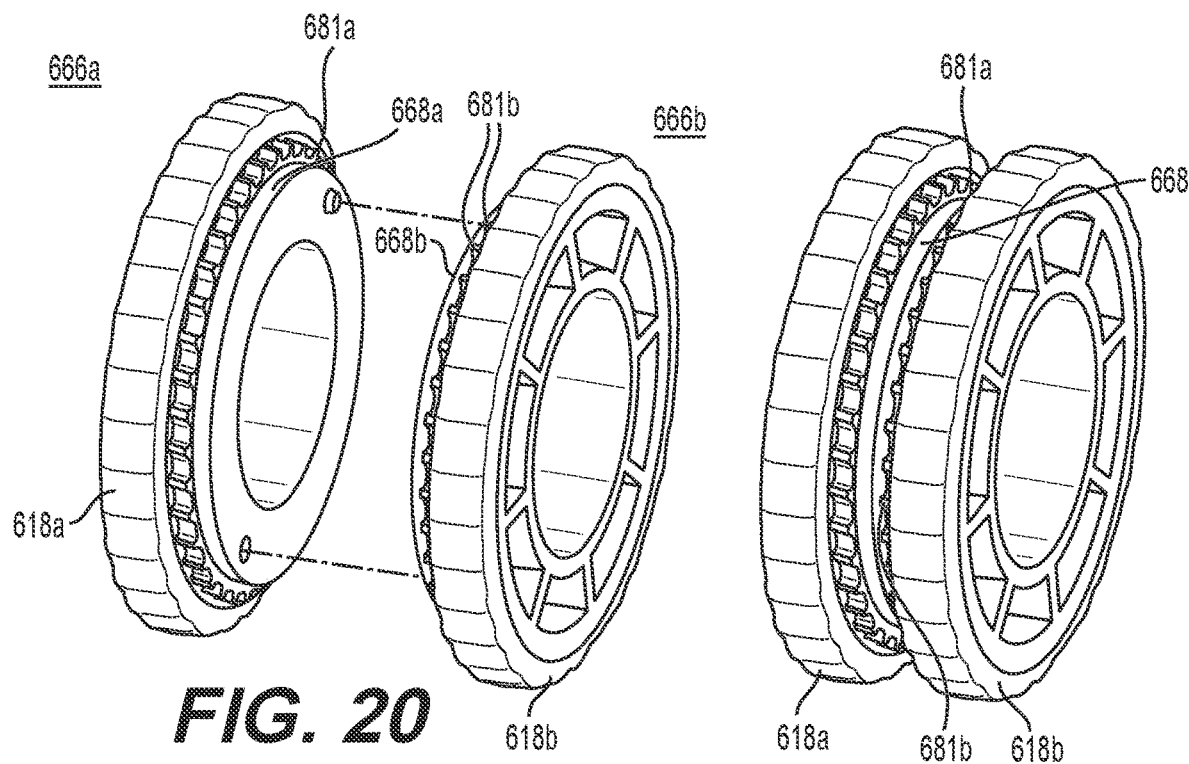
FIG. 20 illustrates an example modular thumbwheel assembly.

FIG. 19 illustrates an exemplary barrel 666 having two sets of teeth 681 with grooves therebetween. Between the two sets of teeth 681, which are arranged around the circumference of a circular cross section, is a surface 668 spacing the sets of teeth 681 apart from one another. As illustrated, the surface is smooth, but is not so limited. Moreover, although a surface is illustrated, the surface is not necessary. The teeth may be spaced apart merely be separating two disks with teeth and/or grooves on the periphery an appropriate distance apart, perhaps with both disks mounted on common axle (not shown). As discussed in detail, above, the barrel assembly 666 may be unitary, or may be unitary with the thumbwheels (not shown in FIG. 19). As illustrated in FIG. 20, the thumbwheel assembly with the barrel 666 may be modular such that a first lateral portion of the barrel 666a and a first lateral portion of the thumbwheel 618a may be unitary and fit together with another unitary piece comprising as second lateral portion of the barrel 666b and a second lateral portion of the thumbwheel 618b. The lateral parts thumbwheel assembly may also include surfaces 668a and 668b that when fitted together form a surface to allow for spacing of the sets of teeth apart from one another.

Figure 21:
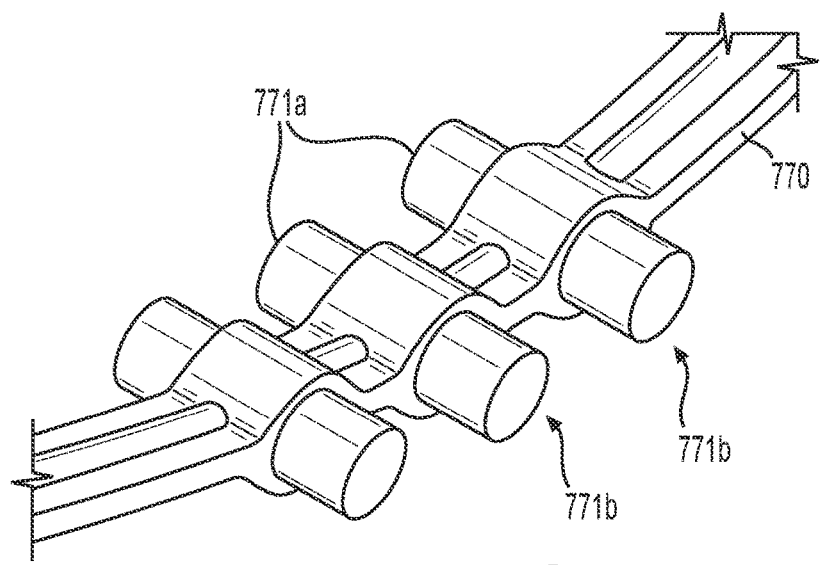
FIG. 21 illustrates an example timing belt with timing belt teeth.

An exemplary timing belt with timing belt teeth are illustrated in FIG. 21. A timing belt for use with the barrel thus described has a plurality of protrusions on opposite sides of the belt, for example, extending perpendicular to a pitch axis of the belt. The belt shown in FIG. 21 is exemplary only, as it only shows three sets of teeth, but the belt is designed to have teeth along enough of the belt to sufficiently deploy the stent.

Figure 22:
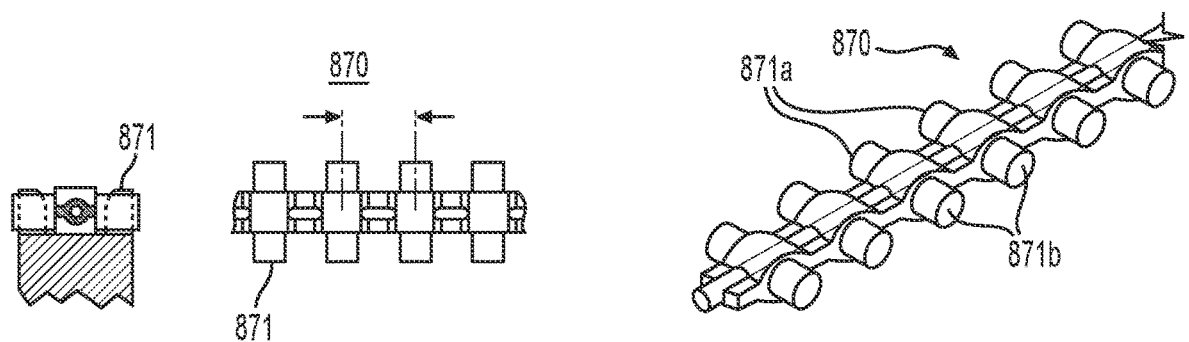
FIG. 22 illustrates an example timing belt with timing belt teeth.

Exemplary belt teeth are shown in FIG. 22. As illustrated in FIG. 22, exemplary belt teeth may have a cylindrical shape with a flat top, e.g., trapezoidal cross-section, to allow for engagement with the barrel teeth. Although a trapezoidal cross section is shown, the teeth are not so limited and may be of any cross section that may engage with the barrel teeth sufficiently to allow belt movement to be actuated by barrel rotation. Other possible shapes, without limitation, include; without limitation, rounded, trapezoidal, cylindrical, diamond, square, triangular or any variation thereof.

FIG. 23A illustrates an idler 1182 that may be used with the posi-drive belt illustrated in FIG. 22. FIG. 23B illustrates a cross-section of the example idler pulley of FIG. 24A with the posi-drive belt.

Figure 24:
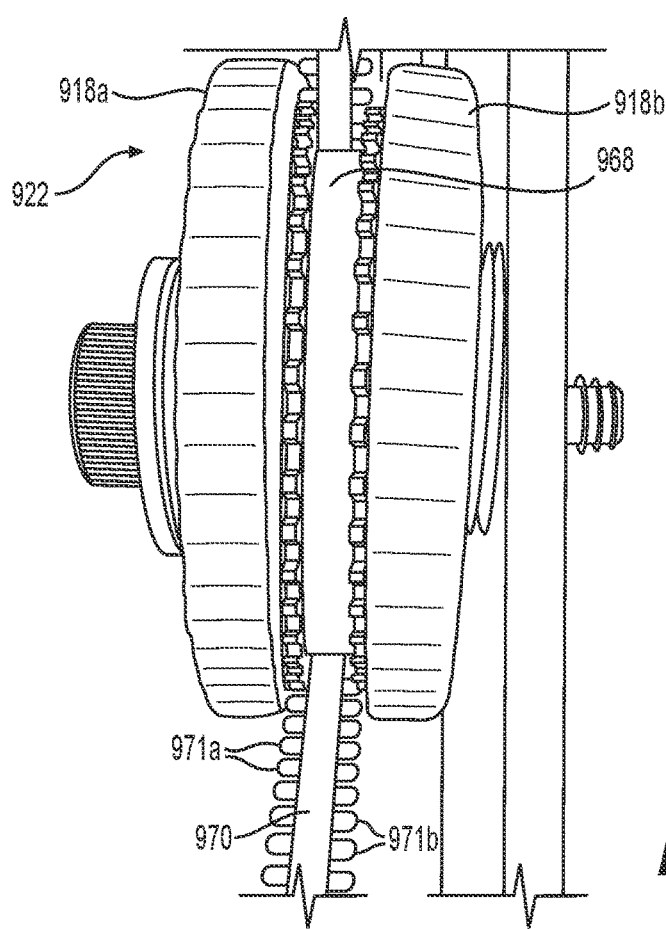
FIG. 24 shows an examplethumbwheel/barrel assembly with a timing belt.

FIG. 24 shows an example thumbwheel/barrel assembly 922 having a cylindrical core 968 and thumbwheel portions 918 with a timing belt 970 having protrusions 971 on two edges of the timing belt 970, such as a single core posi-drive belt. A cylindrical core 968 can be seen between two sets of teeth/grooves 981.

Figure 25:
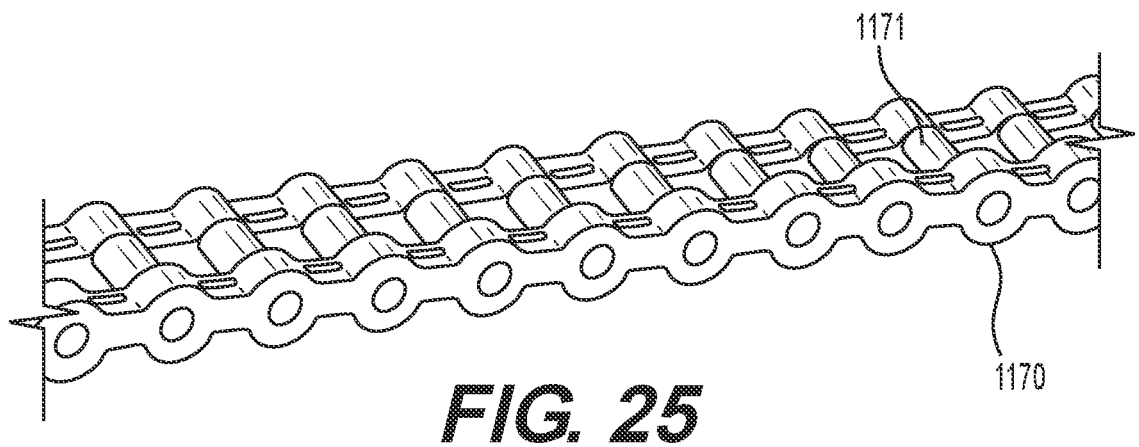
FIG. 25 illustrates an alternative type of posi-drive belt that could be used in the delivery assembly.
Figure 26:
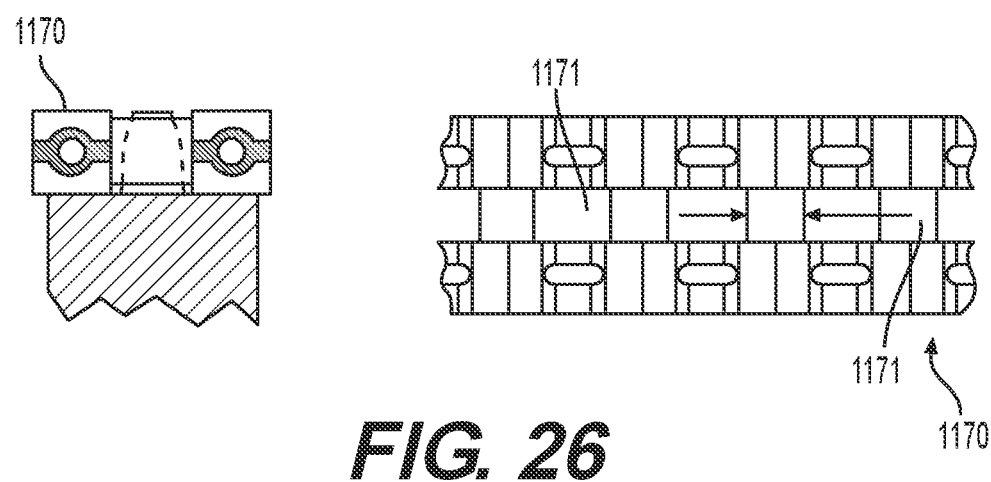
FIG. 26 illustrates an alternative type of posi-drive belt that could be used in the delivery assembly.

FIGS. 25 and 26 illustrate an alternative type of posi-drive belt 1171 that could be used in the example delivery device. The illustrated posi-drive belt 1170 is "twin core" such that there is a recess or opening 1177 between each "crossbar" or tooth 1171 of the belt. The thumbwheel assembly and pulleys described herein may be adapted to engage the openings between the teeth of the belt to perform the movement described herein without impacting the overall function of the delivery device.

Referring again to FIGS. 3A and 3B, the spacing and shape of engagement tooth 319 and additional teeth 335 may be sized appropriately for the type of drive belt used without departing from the spirt and scope of this disclosure.

Figure 27:
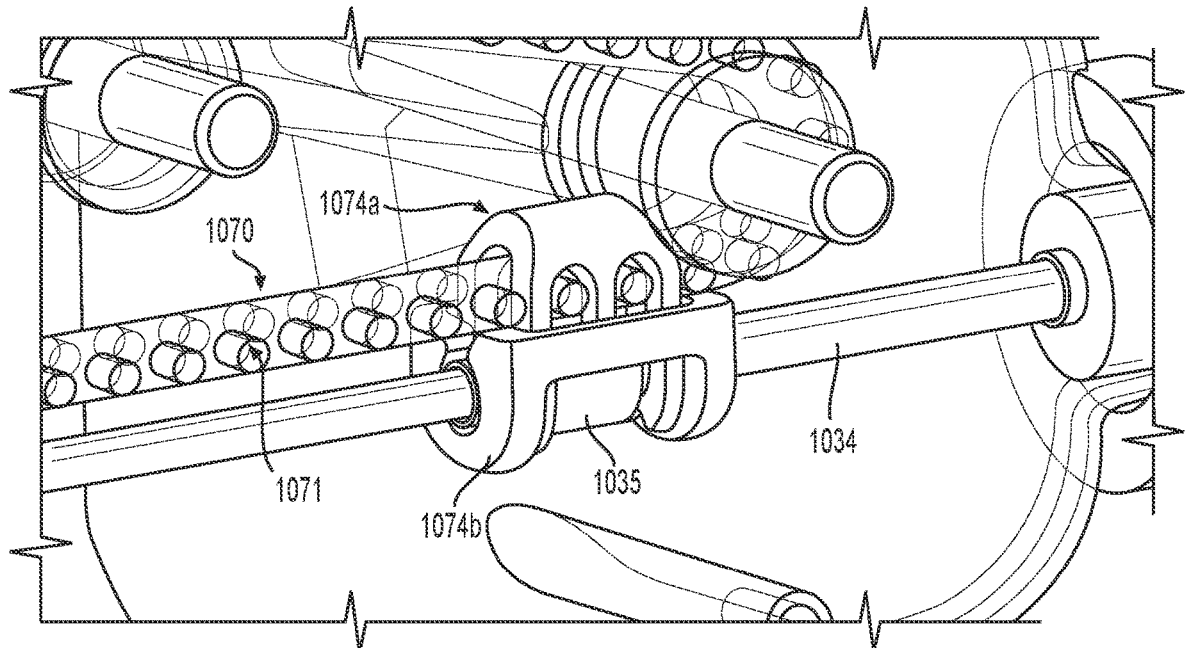
FIG. 27 illustrates an exemplary timing belt link for use with a posi-drive belt.

FIG. 27 illustrates an exemplary timing belt link 1074 for use with a posi-drive belt 1070 in an example delivery handle. As illustrated, the exemplary timing belt link 1074 comprises two parts 1074a and 1074b that can be snapped together. Each part may be injection molded or formed by any appropriate process. The first part 1074a fits over the timing belt teeth 1071 of the timing belt 1070 and snaps around the outer-sheath 1034, trapping a cylindrical feature 1035 affixed to or integral to the outer-sheath 1034. The cylindrical feature 1035 may be integral to the outer sheath 1034 or otherwise affixed to the outer sheath 1034 such that the outer sheath 1034 may move with the movement of the cylindrical feature 1035. The second part 1074b snaps onto the outer sheath 1034 from below to create support system around the first part 1074a to provide rigidity. The second part 1074b provides the strength necessary to withstand deployment forces. The intent is of this design is to allow rotation of the outer sheath 1034 with respect to the belt 1070. According to an aspect of the present design, there is clearance between the timing belt link parts 1074a and 1074b and the outer sheath 1034 and the cylindrical feature 1035 to allow the outer sheath 1034 to spin freely without significant interference from the timing belt link 1074 yet allow linear movement of the timing belt link 1074 to cause movement of the outer sheath 1034 for deployment of the stent (not shown). Such movement is caused by the "entrapment" of the cylindrical feature 1035 by the timing belt link 1074. Thus, the system may remain functional when the distal end of the catheter is fixed and the proximal end (handle) is fully rotated 360° about the axis of the catheter (not shown).

Figure 28:
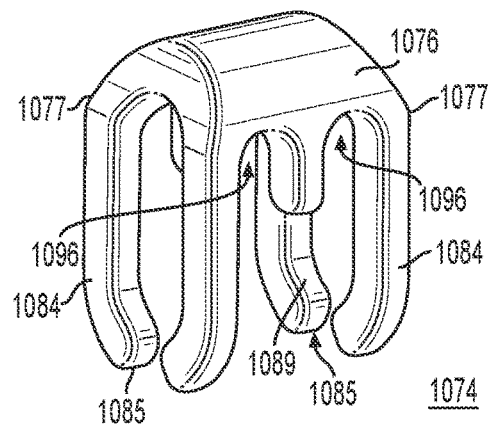
FIG. 28 illustrates an exemplary embodiment of the first part of the timing belt link of FIG. 27.

FIG. 28 illustrates an example of the first part 1074a of the timing belt link 1074a of FIG. 27. The first part 1074a includes an upper body portion 1076; extension arms 1084 extending in a common direction from the upper body portion 1076 and engagement grooves 1096 complimentary to the teeth 1071 of the timing belt 1070. As illustrated, each extension arm 1084 extends from a corner 1077 of the upper body portion 1076, but this the design is not so limited. Distal ends 1085 of the extension arms 1084 may be curved so as to engage around the cylindrical outer sheath 1034, e.g. to provide a rough interference or snap fit. In the illustrated device, there are four extension arms 1084, each extending from a corner 1077 of the upper body portion 1076. The upper body portion 1076 has a long dimension 1087 and a short dimension 1088, where the long dimension 1087 is parallel to the axial direction of the outer sheath 1034 when engaged with the outer sheath 1034 and the short dimension 1088 is roughly perpendicular to the axial direction of the outer sheath 1034 when engaged with the outer sheath 1034. In the exemplary device shown, the engagement grooves 1096 are formed along the long dimension 1087 such that there are at least two grooves 1096 between to extension arms 1085 on one of the long dimensions 1087 of the upper body portion 1076. The grooves 1096 illustrated are U-shaped, such that when there are two such grooves 1096, there is a protrusion 1089 from the upper body 1076 at a location between corners 1077 of the upper body 1076 along the long dimension 1087 of the upper body 1076 forming two grooves 1096. While two grooves 1096 are illustrated, more grooves can be formed by more protrusions from the upper body such that more than two linearly adjacent belt teeth can be engaged. Also, there may be protrusions extending from both long edges/dimensions of the upper body such that grooves on both sides of a posi-drive belt can be engaged. In the presently illustrated device, a longitudinal cross-section of the upper body 1076 may be U-shaped to fit over the outer sheath 1034.

Although not illustrated, the positioning of the extension arms is not limited to being at the corners of the upper body. In other words, as long as the extension arms are sufficient to fit around the outer sheath and grooves to engage the timing belt, the position from which they extend from the outer body can vary. For example, the extension arms may extend from a mid-point of the long dimension of the upper body, while the protrusions may extend from the corner 1077 or end regions of the upper body. Additional protrusions may extend from upper body to allow for additional timing belt teeth to be engaged by the upper body. The timing belt link 1074 may include only the first part but may further include a second part to provide additional strength to the assembly, e.g., to withstand deployment forces.

Figure 29:
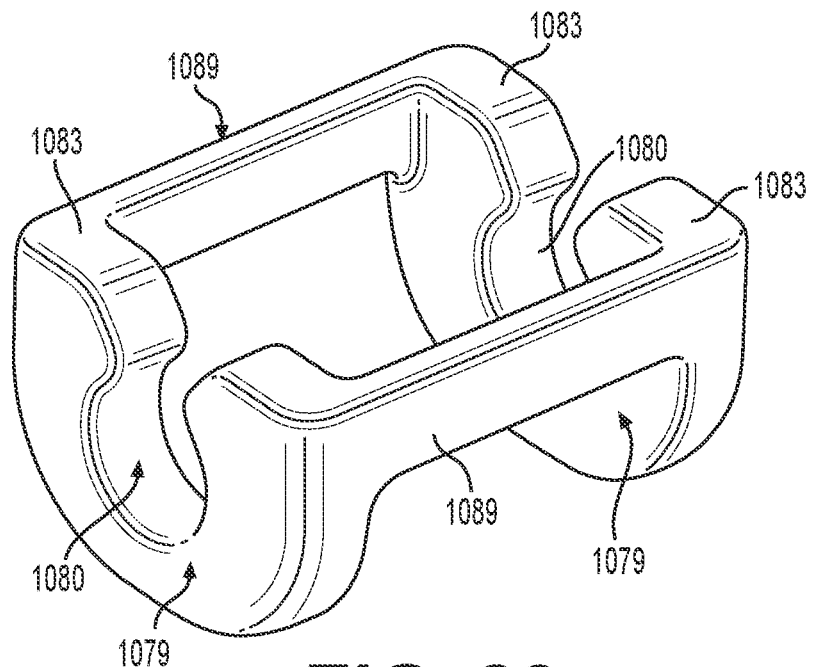
FIG. 29 illustrates an exemplary embodiment of the second part of the timing belt link of FIG. 27.

As shown in FIG. 29, an exemplary second part 1074b of the timing belt link 1074a of FIG. 27, and may include a lower body portion 1075 having two U-shaped end pieces 1079 having a substantially circular center cut out 1080 sized to receive the circumference of the outer sheath 1034. The ends 1083 of each "U" are separated by a distance less than the outer diameter of the outer sheath 134 such that the outer sheath 134 can be pushed into the substantially circular center cut out 1080 of the "U" shaped end 1079. The U-shaped ends 1079 are connected by two upper side rails 1089 extending between upper parts of each of the "U"s 1079 to connect the two end pieces 1079.

The outer sheath 1034 can thus be coupled to the drive belt 1070 by the first part 1074a of the timing link 1074 extending over an upper portion of the outer sheath 1034 with the extension arm ends 1085 extending under a lower portion of the outer sheath 1034. The second part 1074b of the timing belt link 1074 is located over the extension arms 1084 of the first part and snap fit around the outer sheath 1034 by inserting the outer sheath 1034 into the substantially circular center cut outs 1080 of the U-shaped ends 1079 of the second part 1074b. The outer sheath 1034 may further include a cylindrical body 1035 sized to be between the extension arms 1085 of the upper body 1076 when the upper body 1076 is on the outer sheath 1034. For example, the cylindrical body 1035 may be permanently fixed to the outer sheath 1034 and thus be engaged by the timing belt link 1074 to hold the timing belt link 1074 in appropriate position with respect to the outer sheath 1034.

Figure 30:
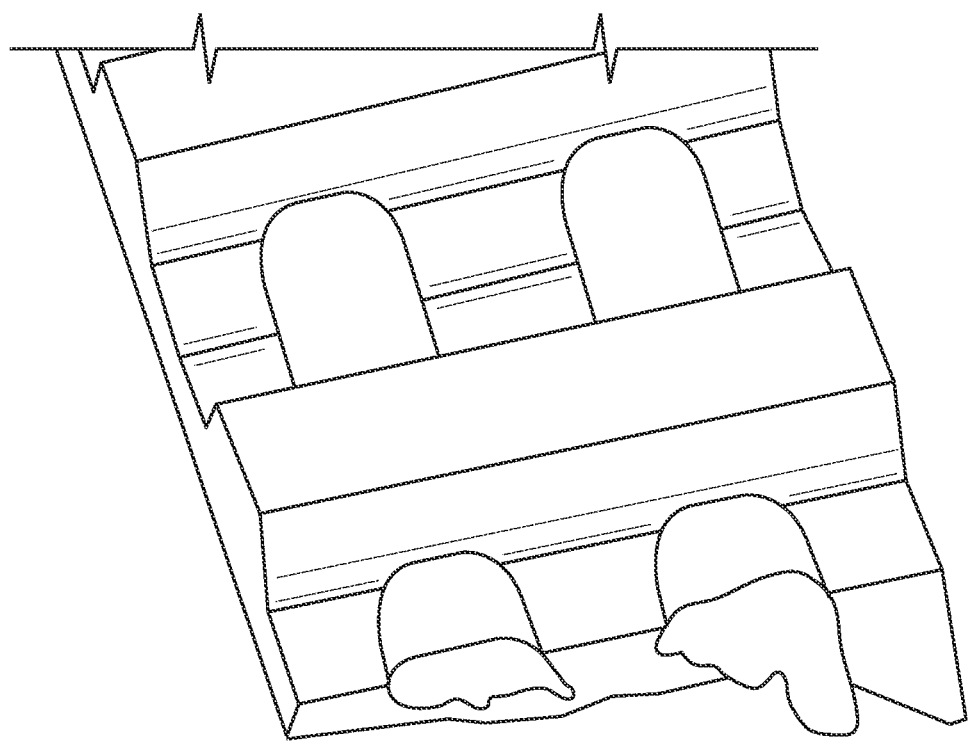
FIGS. 30, 31 and 32 are photographs showing the chord structure of an example posi-drive belt, which may be used in a wheel actuated delivery device.
Figure 31:
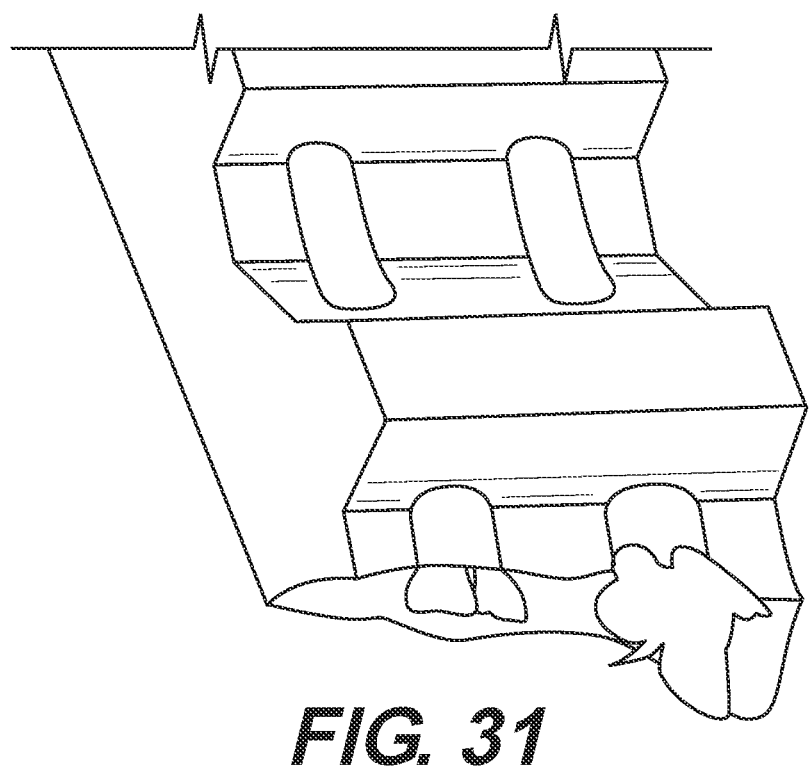
Figure 32:
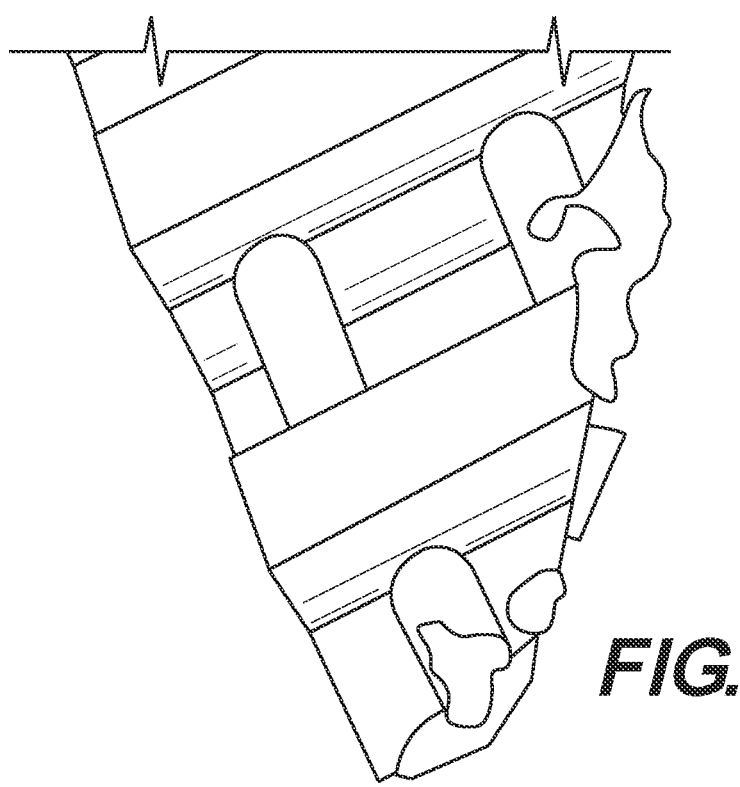

FIGS. 30, 31 and 32 show the chord structure of an example posi-drive belt, which may be used in the example delivery device.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments but should be defined only in accordance with the following claims and their equivalents.

What is claimed is:

1. A kit, comprising:
a wheel actuated device, comprising:
 a wheel having a plurality of teeth with grooves therebetween around at least a portion of the circumference of the wheel;
 an axle about which the wheel is movable; and
 a housing, the wheel at least partially within the housing and having a portion of the wheel extending above the housing;
and
a removable wheel lock, comprising:
 a body;
 an arm connected to and extending from the body, the arm comprising a bent portion and an extending portion, such that arm is movable toward and away from the body;
 an engagement tooth extending from the arm and received in at least one of the grooves between two of the teeth of the wheel; and
 a tab operatively connected to the engagement tooth such that motion of the tab causes the engagement tooth to disengage from the plurality of teeth of said wheel.

2. The kit of claim 1, wherein the removable wheel lock further comprises at least additional teeth operatively connected to the body, the additional teeth sized to be received in said grooves between said plurality of teeth of the wheel.

3. The kit of claim 2, wherein the additional teeth are spaced apart from the engagement tooth along the body.

4. The kit of claim 2, wherein the removable wheel lock further comprises a bridge extending from and adjacent to the body, wherein the additional teeth extend from a portion of the bridge.

5. The kit of claim 4, wherein the bridge of the removable wheel lock further comprises a living hinge.

6. The kit of claim 1, wherein the bent portion of the arm of the wheel lock is a living hinge.

7. The kit of claim 1, wherein the bent portion and the extending portion of the removable wheel lock are a single, unitary structure.

8. The kit of claim 1, wherein the body, the arm, the engagement tooth and the tab of the removable wheel lock are a single, unitary structure.

9. The kit of claim 1, wherein the body of the removable wheel lock is substantially curved.

10. The kit of claim 1, wherein said wheel lock is a single unitary structure.

11. The kit of claim 1, wherein the body has an arc shape, wherein the arc shape traces a semicircle or smaller.

* * * * *